US008192026B2

(12) United States Patent
Gravely et al.

(10) Patent No.: US 8,192,026 B2
(45) Date of Patent: *Jun. 5, 2012

(54) TEAR FILM MEASUREMENT

(75) Inventors: Benjamin T. Gravely, Raleigh, NC (US); Donald R. Korb, Boston, MA (US)

(73) Assignee: TearScience, Inc., Morrisville, NC (US)

( * ) Notice: Subject to any disclaimer, the term of this patent is extended or adjusted under 35 U.S.C. 154(b) by 1207 days.

This patent is subject to a terminal disclaimer.

(21) Appl. No.: 11/900,314

(22) Filed: Sep. 11, 2007

(65) Prior Publication Data

US 2008/0319323 A1 Dec. 25, 2008

Related U.S. Application Data

(63) Continuation-in-part of application No. 11/820,664, filed on Jun. 20, 2007, now Pat. No. 7,758,190.

(51) Int. Cl.
*A61B 3/00* (2006.01)
*A61B 3/10* (2006.01)
(52) U.S. Cl. ........................................ 351/221; 351/200
(58) Field of Classification Search ................ 351/62, 351/200, 206; 514/78, 912, 915; 607/96; 424/78.04
See application file for complete search history.

(56) References Cited

U.S. PATENT DOCUMENTS

| | | |
|---|---|---|
| 4,705,037 A | 11/1987 | Peyman et al. |
| 4,747,683 A | 5/1988 | Doane |
| 4,842,401 A | 6/1989 | Maurice |
| 4,938,584 A | 7/1990 | Suematsu et al. |
| D330,769 S | 11/1992 | Blaha et al. |
| 5,475,452 A | 12/1995 | Kuhn et al. |
| 5,621,523 A | 4/1997 | Oobayashi et al. |
| 5,642,137 A | 6/1997 | Kitazumi |
| 5,647,032 A | 7/1997 | Jutamulia |
| 5,719,659 A | 2/1998 | Suzuki |
| D394,505 S | 5/1998 | Hayashi |
| 5,886,767 A | 3/1999 | Snook |
| 5,988,815 A | 11/1999 | Maus et al. |

(Continued)

FOREIGN PATENT DOCUMENTS

EP 0943288 9/1999

(Continued)

OTHER PUBLICATIONS

Ishida, Reiko et al., "Tear Film with 'Orgahexa Eyemasks' in Patients with Meibomian Gland Dysfunction," Optometry and Visions Science, vol. 85, No. 8, Aug. 2008, pp. E684-E691.

(Continued)

*Primary Examiner* — Ricky Mack
*Assistant Examiner* — Mahidere Sahle
(74) *Attorney, Agent, or Firm* — Withrow & Terranova, PLLC

(57) ABSTRACT

The disclosure comprises a method for measuring the relative thickness of the lipid layer component of the precorneal tear film on the surface of an eye after distribution of the lipid layer subsequent to blinking. Light is directed to the lipid layer of a patient's eye with an illuminator. The illuminator is a broad spectrum light source covering the visible region and is a lambertion light emitter such that the light source is specularly reflected from the lipid layer and undergoes constructive and destructive interference in the lipid layer. The specularly reflected light is collected and focused using a collector such that the interference patterns on the tear film lipid layer are observable. The collector also produces an output signal representative of the specularly reflected light suitable for further analysis, such as projection on to a high resolution video monitor or analysis by or storage in a computer.

55 Claims, 7 Drawing Sheets

U.S. PATENT DOCUMENTS

| | | | |
|---|---|---|---|
| 6,198,540 | B1 | 3/2001 | Ueda et al. |
| 6,236,459 | B1 | 5/2001 | Negahdaripour et al. |
| 6,299,305 | B1 | 10/2001 | Miwa |
| 6,394,603 | B2 | 5/2002 | Miwa et al. |
| 6,447,119 | B1 | 9/2002 | Stewart et al. |
| D465,850 | S | 11/2002 | Takizawa |
| D472,637 | S | 4/2003 | Cooper et al. |
| 6,659,613 | B2 | 12/2003 | Applegate et al. |
| 6,685,320 | B2 | 2/2004 | Hirohara et al. |
| 6,736,507 | B2 | 5/2004 | Kudryashov et al. |
| 7,073,906 | B1 | 7/2006 | Portney |
| 7,121,666 | B2 | 10/2006 | Tseng et al. |
| D552,736 | S | 10/2007 | Yamaoka |
| D582,556 | S | 12/2008 | Yamaoka |
| D607,562 | S | 1/2010 | Heine et al. |
| 7,654,669 | B2 | 2/2010 | Suzuki |
| 7,688,453 | B2 | 3/2010 | Williby et al. |
| 7,758,190 | B2 | 7/2010 | Korb et al. |
| 7,771,353 | B2 | 8/2010 | Luce |
| 8,092,023 | B2 | 1/2012 | Korb et al. |
| 2002/0180929 | A1 | 12/2002 | Tseng et al. |
| 2003/0056281 | A1 | 3/2003 | Hasegawa |
| 2004/0212781 | A1 | 10/2004 | Mihashi et al. |
| 2006/0055956 | A1 | 3/2006 | Takahashi et al. |
| 2006/0109423 | A1 | 5/2006 | Wang |
| 2006/0140454 | A1 | 6/2006 | Northcott et al. |
| 2008/0273171 | A1 | 11/2008 | Huth et al. |
| 2009/0201465 | A1 | 8/2009 | Huth |
| 2009/0225276 | A1 | 9/2009 | Suzuki |
| 2010/0259721 | A1 | 10/2010 | Korb et al. |
| 2011/0273550 | A1 | 11/2011 | Amano et al. |

FOREIGN PATENT DOCUMENTS

| | | |
|---|---|---|
| EP | 1900320 A1 | 3/2008 |
| EP | 2189108 A1 | 5/2010 |
| GB | 2407378 B | 9/2006 |
| JP | 8052112 | 2/1996 |
| JP | 2007523382 A | 8/2007 |
| JP | 2009134276 A | 6/2009 |
| WO | 0026614 | 5/2000 |
| WO | WO2005/044099 A1 | 5/2005 |
| WO | 2008137863 A2 | 11/2008 |

OTHER PUBLICATIONS

Blackie, Caroline et al., "The Relationship Between Dry Eye Symptoms and Lipid Layer Thickness," Cornea, vol. 28, No. 7, Aug. 2009, pp. 789-794.

Rolando, Maurizio et al., "New Test to Quantify Lipid Layar Behavior in Healthy Subjects and Patients with *Keratoconjunctivitis sicca*," Cornea, vol. 27, No. 8, Sep. 2008, pp. 866-870.

Prydal, Jeremy I. et al., "Study of Human Precorneal Tear Film Thickness and Structure Using Laser Interferometry," Investigative Ophthalmology & Visual Science, vol. 33, No. 6, May 1992, pp. 2006-2011.

Korb, Donald R. et al., "Meibomian Gland Diagnostic Expressibility: Correlation With Dry Eye Symptoms and Gland Location," Cornea, vol. 27, No. 10, Dec. 2008, pp. 1142-1147.

Guillon, Jean-Pierre, "Non-Invasive Tearscope Plus Routine for Contact Lens Fitting," Contact Lens and Anterior Eye, (Supplement) 21, 1998, pp. S31-S40.

Guillon, Jean-Pierre, "Use of the Tearscope Plus and Attachments in the Routine Examination of the Marginal Dry Eye Contact Lens Patient," Lacrimal Gland, Tear Film, and Dry Eye Syndrome 2, 1998, pp. 859-867.

Hosaka, Eri et al., "Interferometry in the Evaluation of Precorneal Tear Film Thickness in Dry Eye," American Journal of Opthalmology, vol. 151, No. 1, Jan. 2011, pp. 18-23.

Arndt, G. Dickey et al., "Microwave Treatment of Prostate Cancer and Hyperplasia," NASA Tech Briefs, Jun. 2005, 1 page.

King-Smith, P. Ewen et al., "The Thickness of the Human Precorneal Tear Film: Evidence from Reflection Spectra," Investigative Ophthalmology & Visual Science, Oct. 2000, vol. 41, No. 11, 12 pages.

Nichols, Jason J. et al., "The Thickness of the Post-Lens Tear Film Measured by Interferometry," Lacrimal Gland, Tear Film, and Dry Eye Syndromes 3, Edited by D. Sullivan et al., Kluwer Academic / Plenum Publishers, 2002, 5 pages.

Alonso-Caneiro, D. et al., "Context-Based Modelling of Interferometric Signals for the Assessment of Tear-Film Surface Quality," 2009 IEEE/SP 15th Workshop on Statistical Signal Processing (SSP), 2009, pp. 553-556.

Korb, Donald, "Survey of Preferred tests for Diagnosis of the Tear Film and Dry Eye," Cornea, vol. 19, 2000, pp. 483-486.

Finnemore, VM et al., "Flourescein Dye Concentration as a Factor in Tear Film Flourescence," in Sullivan DA (ed): Lacrimal Gland, Tear Film and Dry Eye Syndromes: Basic Science and Clinical Relevance, Adv. Exp. Med. Biol., No. 438, 1998, pp. 875-878.

Kimball, S., et al., "Evidence for the major contribution of evaporation to tear film thinning between blinks," Investigative Ophthalmology and Visual Science, vol. 51, No. 12, Dec. 2010, http://www.iovs.org/content/51/12/6294.full.pdf+html, pp. 6294-6297.

King-Smith, P. Ewen, et al., "Application of a novel interferometric method to investigate the relation between lipid layer thickness and tear film thinning," Investigative Ophthalmology and Visual Science, vol. 51, No. 5, May 2010, http://www.iovs.org/content/51/5/2418.full.pdf+html, pp. 2418-2423.

Szczesna, D., et al., "Predicting dry eye using noninvasive techniques of tear film surface assessment," Investigative Ophthalmology and Visual Science, vol. 52, No. 2, Feb. 2011, http://www.iovs.org/content/52/2/751.full.pdf+html, pp. 751-756.

Veres, A., et al., "Imaging lid-parallel conjunctival folds with OCT and comparing its grading with the slit lamp classification in dry eye patients and normal subjets," Investigative Ophthalmology and Visual Science, vol. 52, No. 6, May 2011, http://www.iovs.org/content/52/6/2945.full.pdf+html, pp. 2945-2951.

Pimenidi, M.K., et al., "Meibomian Gland Disfunction in Computer Vision Syndrome (abstract)," Annals of Ophthalmology (Vestn Oftalmol.) (Russia), Nov.-Dec. 2010, 126(6), http://www.medlit.ru/medeng/vof/vof10e0649.htm, 3 pages.

Behrens, Ashley, MD, "Multiwave Interferometry is Creating a New Understanding of the Tear Film," Refractive Eyecare, Oct. 2009, from www.refractiveeyecare.com, 5 pages.

An, Yang et al., "Contrast Sensitivity Measurement in Dry Eyes," Int J Ophthalmol, vol. 10, No. 3, Mar. 2010, pp. 488-491.

Rolando, M. et al., "New Test to Quantify Lipid Layer Behavior in Healthy Subjects and Patients with *Keratoconjunctivitis sicca*," Cornea, vol. 8, No. 27, Sep. 2008, pp. 866-870.

Uchida, A. et al., "Nonivasive Interference Tear Meniscometry in Dry Eye Patients with Sjogren Syndrome," Am. J. Ophthalmol., vol. 144, No. 2, Aug. 2007, pp. 232-237.

Behrens, Ashley, MD, "Interferometry for the Detection of Dry Eye," Cataract & Refractive Surgery Today Europe, Nov./Dec. 2008. pp. 57-58.

Lopez Garcia, J.S. et al., "Measure of the Fatty Layer Thickness of Precorneal Tear Film by Interference Colours in Different Types of Dry Eye," Sociedad Espanola de Oftalmologia, vol. 78, Part 5, Jan. 2003, pp. 257-264.

Prydal, J.I. et al., "Study of Precorneal Tear Film Thickness and Structure by Interferometry and Confocal Microscopy," Investigative Ophthalmology and Visual Science, vol. 33, No. 6, May 1992, pp. 1996-2005.

Prydal, J.I. et al., "In Vivo Confocal Microscopy of the Cornea and Tear Film," Scanning, vol. 17, 1995, pp. 133-135.

Mathers, W.D., "Assessment of the Tear Film with Tandem Scanning Confocal Microscopy," Cornea, vol. 16, No. 2, 1997, pp. 162-168.

Kaisheva, M et al., "Thin Liquid Films from Water-Based Dispersions of Cellulose Acethophthalate in the Presence of Pilocarpine Hydrochloride," J. Dispersion Sci. Technol., 1997.

Licznerski, T.J. et al., "Application of Twyman-Green Interferometer for Evaluation of in Vivio Breakup Characteristic of the Human Tear Film," Journal of Biomedical Optics, vol. 4, No. 1, Jan. 1999, pp. 176-182.

Licznerski, T.J. et al., "Interference and Model Study of the Human Tear Film," Politechnika Wroclawska, Source DAI-C 60/04, Winter 1999, p. 782 (Abstract only).

Patel, S. et al., "Corneal Sensitivity and Some Properties of the Tear Film After Laser in Situ Keratomileusis,"Journal of Refractive Surgery, Vo. 17, No. 1, 2001, pp. 17-24.

Kowalik, W. et al., "Corneal Topography Measurement of the Eye by Means of Radial Shearing Interferometer," Proc. SPIE—Int. Soc. Opt. Eng. vol. 4356, 2001. pp. 375-380.

Hellmuth, T. et al., "Non-Contact Measurement of the Optical Imaging Quality of an Eye," Proc. SPIE—Int. Soc. Opt. Eng. vol. 4431, 2001, pp. 52-58.

Garncarz, B.E. et al., "Corneal Topography Measurement by Means of Radial Shearing Interference II—Experiment Results," Optik, vol. 113, No. 1, 2002, pp. 46-50.

Tseng, S.C. et al., "Changes of Lipid Tear Film in Dry Eye Patients and Normal Subjects Following One Drop of a New Emulsion Eye Drop Using Kinetic Analysis of Tear Interference Images," ARVO, vol. 44, 2003, E-Abstract 2457, 2 pages.

King-Smith, P.E. et al., "Can the Mucus Layer of the Tear Film be Demonstrated by Interferometry?," IOVS, vol. 45, Supp. 2, Apr. 2004, E-Abstract 3882. 2 pages.

Paugh, J.R. et al., "White Light Tear Film Interferometry in Dry Eye Sub-Types," IOVS, vol. 45, Supp. 1, Apr. 2004, E-Abstract 93, 2 pages.

Elizondo, A.E. et al., "Detection of Blink Related Microtrauma by Kinetic Analysis of Tear Interference Images in Patients with Steven Johnson Syndrome and Toxic Epidermal Necrolysis Syndrome," IOVS, vol. 46, Supp. S, 2005, E-Abstract 2654, 2 pages.

King-Smith, P.E. et al., "Human Tear Film Breakup Studied by a New Imaging Interferometer: Preliminary Observations," IOVS, vol. 46, Supp. S, 2005, E-Abstract 4400, 2 pages.

Scaffidi, R.C. et al., "Lipid Layer Thickness and Dry Eye Symptoms," IOVS, vol. 46, Supp. S, 2005, E-Abstract 4444, 2 pages.

Korb, D. et al., "Lipid Layer Thickness Changes Following the Instillation of Two Novel Lubricant Eye Drops," IOVS, vol. 46, Supp. S, 2005, E-Abstract 2036, 2 pages.

Rolando, M. et al., "The Dynamic Lipid Interference Pattern (DLIP) Test in Normal and Dry Eyes," IOVS, vol. 46, Supp. S, 2005, E-Abstract 4422, 2 pages.

Dogru, M. et al., "Strip Meniscometry: A New and Simple Method of Tear Meniscus Evaluation," Invest. Ophthalmol. Vis. Sci., vol. 47, No. 5, May 2006, pp. 1895-1901.

Dogru, M. et al., "New Insights into the Diagnosis and Treatment of Dry Eye," Ocular Surface, vol. 2, No. 2, 2004, pp. 59-74.

Szczesna, D. et al., "Numerical Analysis of Interferograms of Tear Film Build-Up Time," Ophthalmic and Physiological Optics, vol. 29, No. 3, May 2009, pp. 211-218.

McDonald, J.E. "Surface Phenomena of the Tear Film" Am J Ophthalmol 67:56-64; 1968.

Norn, M.S. "Semiquantitative Interference Study of Fatty Layer of Precorneal Film" Acta Ophthalmol 57:766-74; 1979.

Guillon, J.P. "Tear Film Photography and Contact Lens Wear" J Br Contact Lens Assoc 5:84-7; 1982.

Kilp, H. et al., "Tear Film Observation by Reflecting Microscopy and Differential Interference Contrast Microscopy" from the Preocular Tear Film in Health, Disease, and Contact Lens Wear, Lubbock, TX, Dry Eye Institute, 564-9; 1986.

Guillon, J.P. "The Tear Film Structure of the Contact Lens Wearer" PhD Thesis, The City University Department of Optometry and Visual Science; 1987.

Young, G. et al., "Characteristics of the Pre-Lens Tear Films During Hydrogel Contact Lens Wear" Ophthalmic Physiol. Opt. 11:53-58; 1991.

Mathers, W.D. "Ocular Evaporation in Meibomian Gland Dysfunction and Dry Eye" Ophthalmol 100:347-51; 1993.

Korb, D.R. et al., "Tear Film Lipid Layer Thickness as a Function of Blinking" Cornea 13:354-9;1994.

Korb, D.R. et al., "Increase in Tear Film Lipid Layer Thickness Following Treatment of Meibomian Gland Dysfunction" Adv Exp Med Biol 350:293-8; 1994.

Korb, D.R. et al., "Effect of Periocular Humidity on the Tear Film Lipid Layer" Cornea 15:129-34;1996.

Yokoi, N. et al., "Correlation of Tear Lipid Layer Interference Patterns with the Diagnosis and Severity of Dry Eye" American Journal of Ophthalmology 122(6):818-824; Dec. 1996.

Craig, J.P. et al., "Importance of the Lipid Layer in Human Tear Film Stability and Evaporation" Optom Vis Sci; 74:8-13; 1997.

Guillon, J.P. et al., "Preocular Tear Film Characteristics of Nonwearers and Soft Contact Lens Wearers" Optom Vis Sci 74:273-9; 1997.

Tearscope "Tearscope Plus Clinical Hand Book and Tearscope Plus Instructions" Windsor, Keeler Ltd., Berkshire, Keeler Insts Inc., Broomall, PA; 1997.

McCarty, C.A. et al., "The Epidemiology of Dry Eye in Melbourne, Australia" Ophthalmol 105:1114-9; 1998.

Pflugfelder,S.C. et al., "Evaluation of Subjective Assessments and Objective Diagnostic Tests for Diagnosing Tear-Film Disorders Known to Cause Ocular Irritation" Cornea 17:38-56; 1998.

Yokoi, N. et al., "Assessment of Meibomian Gland Function in Dry Eye Using Meibometry" Arch. Ophthalmol. 117:723-9; 1999.

Korb, D.R. "Alleviation of Computer-Induced Eye Discomfort Syndrome and Associated Lipid Layer Changes" Adv Exp Med Biol 506(PT A):501-6; 2002.

Korb, D.R. "The Tear Film—Its Role Today and in the Future" from the Tear Film: Structure, Function and Clinical Examination, Butterworth-Heinemann, 126-92; 2002.

Begley, C.G. et al., "The Relationship Between Habitual Patient-Reported Symptoms and Clinical Signs Among Patients with Dry Eye of Varying Severity" Invest. Ophthalmol Vis Sci.; 44:4756-61; 2003.

Goto, E. et al., "Tear Evaporation Dynamics in Normal Subjects and Subjects with Obstructive Meibomian Gland Dysfunction" Invest. Ophthalmol. Vis. Sci. 44:533-9; 2003.

Goto, E. et al., "Differentiation of Lipid Tear Deficiency Dry Eye by Kinetic Analysis of Tear Interference Images" Arch Ophthalmol 121:173-80; 2003.

Foulks G.N. et al., "Meibomian Gland Dysfunction: a Clinical Scheme for Description, Diagnosis, Classification, and Grading" Ocul Surf. 1:107-26; 2003.

Isreb, M.A. et al., "Correlation of Lipid Layer Thickness Measurements with Fluorescein Tear Film Breakup Time and Schirmer's Test" Eye 17:79-83; 2003.

Bron, A.J. et al., "The Contribution of Meibomian Disease to Dry Eye" Ocul Surf 2:149-65; 2004.

Bron, A.J. et al., "Functional Aspects of the Tear Film Lipid Layer" Exp Eye Res. 78:347-60; 2004.

DiPascuale R.W. et al., "Sequential Changes of Lipid Tear Film After the Instillation of a Single Drop of a New Emulsion Eye Drop in Dry Eye Patients" Ophthalmology 111:783-91; 2004.

Nichols, K.K. et al., "The Repeatability of Clinical Measurements of Dry Eye" Cornea 23:3 272-285; Apr. 2004.

Nichols, K.K. et al., "The Lack of Association Between Signs and Symptoms in Patients with Dry Eye Disease" Cornea 23:762-70; 2004.

Yokoi, N. et al., "New Instruments for Dry Eye Diagnosis" Semin Ophthalmol vol. 20, No. 2, pp. 63-70; Apr.-Jun. 2005.

Licznerski, T.J. et al., "Novel Double Path Shearing Interferometer in Corneal Topography Measurements" Proceedings of the SPIE—The International Society for Optical Engineering, vol. 5959, No. 1, Sep. 16, 2005.

Szczesna, D.H. et al., "Interferometric Measurements of the Tear Film Irregularities on the Human Cornea" Proceedings of the SPIE—The International Society for Optical Engineering, vol. 5959, No. 1, Sep. 16, 2005.

Goto, E. et al., "Successful Tear Lipid Layer Treatment for Refractory Dry Eye in Office Workers by Low-Dose Lipid Application on the Full-Length Eyelid Margin" American Journal of Ophthalmology 142(2) 264-270, Aug. 2006.

Foulks G.N., "The Correlation Between the Tear Film Lipid Layer and Dry Eye Disease" Survey of Ophthalmology 52 (4) 369-374, Jul.-Aug. 2007.

"Report of the International Dry Eye Workshop" Ocul. Surf. 5(April):69-70; 2007.

Schaumberg, D.A. et al., "Development and Validation of a Short Global Dry Eye Symptom Index" Ocul. Surf. 5 (1):50-57; 2007.

Kojima, Takashi et al., "A New Noninvasive Tear Stability Analysis System for the Assessment of Dry Eyes," Investigative Ophthalmology & Visual Science, May 2004, vol. 45, No. 5, pp. 1369-1374.

Wu, Dijia et al., "Texture Based Prelens Tear Film Segmentation in Interferometry Images," Machine Vision and Applications, vol. 21, No. 3, Apr. 2010, pp. 253-259.

Szczesna, Dorota H., et al., "Lateral Shearing Interferometry for Analysis of Tear Film Surface Kinetics," Optom. Vis. Sci., vol. 87, No. 7, Jul. 2010, pp. 513-517.

Wu, Dijia et al., "Sign Ambiguity Resolution for Phase Demodulation in Interferometry with Application to Prelens Tear Film Analysis," 2010 IEEE Computer Society Conference on Computer Visions and Pattern Recognition, CVPR 2010, 2010, pp. 2807-2814.

Berliner, M. L., M.D., "The Margins of the Eyelid" Chapter Eight, Biomicroscopy of the Eye, Slit Lamp Microscopy of the Living Eye, vol. 1, Medical Book Department of Harper & Brothers, NYC, Paul B. Hoeber, Inc., 1949, 5 pages (pp. 252-257).

Miller, David "Pressure of the Lid on the Eye" Arch. Opthalmology, vol. 78, 1967, 7 pages (pp. 382-330).

Korb, Donald R., O.D. et al., "The Phenomenon of Central Circular Clouding; the loss of corneal transparency unique to contact lens practice requiring specialized techniques for early recognition" Journal of American Optometric Association, vol. 39, No. 3, Mar. 1968, 8 pages (pp. 223-230).

McDonald, James E., M.D., "Surface Phenomena of Tear Films" Tr. Am. Ophth. Soc., vol. 66, 1968, 35 pages (pp. 905-939).

Norn, M. S., "Semiquantitative Interference Study of Fatty Layer of Precorneal Film" ACTA Ophthalmologica, vol. 57, 1979, 9 pages (pp. 766-774).

Korb, Donald R., O.D., et al., "Meibomian Gland Dysfunction and Contact Lens Intolerance" Jnl American Optometric Association, vol. 51, No. 3, Mar. 1980, 9 pages (pp. 243-251).

Author Unknown, "Measurement of Intraocular Pressure" Biomedical Foundations of Ophthalmology, Intraocular Pressure, vol. 2, Chapter 7, Circa 1982, 6 pages (pp. 11-16).

Guillon, Jean-Pierre, BSc, FBCO, FBOA, FSMC, "Tear Film Photography and Contact Lens Wear" Journal of the British Contact Lens Association, 1982, 3 pages (pp. 84-87).

Ernest, J. Terry, M.D. et al., "Ocular Massage Before Cataract Surgery" Tr. Am. Ophth. Soc., vol. LXXXIII, 1985, 13 pages (pp. 205-217).

Olsen, Thomas, "Reflectometry of the Precorneal Film" ACTA Ophthalmologica, vol. 63, 1986, 7 pages (pp. 432-438).

Leibovitch, Larry S., Ph.D., "The Shape of the Eye: Why the Eye is Round" Florida Atlantic University, Boca Raton, FL, Circa 1986, 28 pages (pp. 1-27).

Kilp, Helmuth, et al., "Tear Film Observation by Reflecting Microscopy and Differential Interference Contrast Microscopy" The Precorneal Tear Film, Dry Eye Institute, Inc., Lubbock, TX, 1986, 7 pages (pp. 564-569).

Carrington, S. D., et al., "Polarized Light Biomicroscopic Observations on the Pre-Corneal Tear Film" J. Small Anim. Pract., vol. 28, 1987, 20 pages (pp. 605-622).

Guillon, Jean-Pierre Charles Francois, "Tear Film Structure of the Contact Lens Wearer" Ph.D. Thesis, The City University, London, 1987, 398 pages.

Doane, Marshall G., "An Instrument for in Vivo Tear Film Interferometry" (and critique of same), Optometry and Vision Science, vol. 66, No. 6, 1989, 10 pages (pp. 383-388).

Ong, B. L., et al., "Meibomian Gland Dysfunction: Some Clinical, Biochemical and Physical Observations" Ophthal. Physiol. Opt., vol. 10, Apr. 1990, 5 pages (pp. 144-148).

Danjo, Yukitaka, et al., "Measurement of the Precorneal Tear Film Thickness with a Non-Contact Optical Interferometry Film Thickness Measurement System" Jpn J Ophthal., vol. 38, 1994, 7 pages (pp. 260-266).

Doane, Marshall G., "Abnormalities of the Structure of the Superficial Lipid Layer on the in Vivo Dry-Eye Tear Film" (and critique of same) Lacrimal Gland, Tear Film, and Dry Eye Syndromes, Plenum Press, New York, 1994, 11 pages (pp. 489-493).

Korb, Donald R. et al., "Increase in Tear Film Lipid Layer Thickness Following Treatment of Meibomian Gland Dysfunction" Lacrimal Gland, Tear Film and Dry Eye Syndromes: Basic Science Clinical Relevance. Adv. Exp. Med. Biol., vol. 350, 1994, 6 pages (pp. 293-298).

Korb, Donald R., O.D., et al., "Tear Film Lipid Layer Thickness as a Function of Blinking" Cornea, vol. 13(4), Raven Press, Ltd., New York, 1994, 6 pages (pp. 354-359).

Greiner, Jack V., et al., "Meibomian Gland Phospholipids" Current Eye Research, Oxford University Press, 1995, 5 pages (pp. 371-375).

Greiner, Jack V., et al., "Volume of the Human and Rabbit Meibomian Gland System" Lacrimal Gland, Tear Film, and Dry Eye Syndromes 2, Plenum Pres, New York, 1998, 5 pages (pp. 339-343).

Driver, Paul J., et al., "Meibomian Gland Dysfunction" Major Review, Survey of Ophthalmology, vol. 40, No. 5, Mar.-Apr. 1996, 25 pages (pp. 343-367).

Korb, Donald R., O.D., et al., "Effect of Periocular Humidity on the Tear Film Lipid Layer" Cornea, vol. 15(2), 1996, 6 pages (pp. 129-134).

Korb, Donald R., et al., "Tear Film Lipid Layer Formation: Implications for Contact Lens Wear" Review, Optometry and Vision Science, vol. 73, No. 3, 1996, 4 pages (pp. 189-192).

Yokoi, Norihiko, MD, PhD, et al., "Correlation of Tear Lipid Layer Interference Patters with the Diagnosis and Severity of Dry Eye" American Journal of Ophthalmology, vol. 122, Dec. 1996, 7 pages (pp. 818-824).

Bron, Anthony J., BSc, FRCS, FCOphth, et al., "The Ocular Appendages: Eyelids, Conjunctiva and Lacrimal Apparatus" Chapter 2, Wolff's Anatomy of the Eye and Orbit, Eighth Edition, Chapman & Hall Medical, Jan. 1997, 12 pages (pp. 30-42).

Fogt, Nick, et al., "Interferometric Measurement of Tear Film Thickness by use of Spectral Oscillations" J. Opt. Soc. Am. A., vol. 15, No. 1, Jan. 1998, 8 pages (pp. 268-275).

Lieznerski, Tomasz J., et al., "Analysis of Shearing Interferograms of Tear Film Using Fast Fourier Transforms" Journal of Biomedical Optics, vol. 3, No. 1, Jan. 1998, 6 pages (pp. 32-37).

Doane, Marshall G., et al., "Tear Film Interferometry as a Diagnostic Tool for Evaluating Normal and Dry-Eye Tear Film" Lacrimal Gland, Tear Film, and Dry Eye Syndromes 2, Plenum Press, New York, 1998, 7 pages (pp. 397-303).

Greiner, Jack V., et al., "Effect of Meibomian Gland Occlusion on Tear Film Lipid Layer Thickness" Lacrimal Gland, Tear Film, and Dry Eye Syndromes 2, Plenum Press, New York, 1998, 4 pages (pp. 345-348).

Hayreh, Sohan Singh, et al., "Parapapillary Chorioretinal Atrophy in Chronic High-Pressure Experimental Glaucoma in Rhesus Monkeys" Investigative Ophthalmology & Visual Science, vol. 39, No. 12, Nov. 1998, 8 pages (pp. 2296-1303).

Hickson, Ian, "The Eye" Ian Hickson's Description of the Eye, http://academia.hixie.ch/bath/eye/home.html, 1998, 11 pages.

Korb, Donald R., et al., "Human and Rabbit Lipid Layer and Interference Pattern Observations" Lacrimal Gland, Tear Film, and Dry Eye Syndromes 2, Plenum Press, New York, 1998, 4 pages (pp. 305-308).

Sullivan, David A., et al., "Androgen Regulation of the Meibomian Gland" Lacrimal Gland, Tear Film, and Dry Eye Syndromes 2, Plenum Press, New York, 1998, 5 pages (pp. 327-331).

Mori, Asako, M.D., et al., "Efficacy and Safety of Infrared Warming of the Eyelids" Cornea, vol. 18(2), 1999, 6 pages (pp. 188-193).

Korb, Donald R., et al., "The Tear Film" Structure, Function and Clinical Examination British Contact Lens Association, Butterworth Heinemann, Circa 1999, 15 pages (pp. 154-179).

King-Smith, P. Ewen, et al., "Three Interferometric Methods for Measuring the Thickness of Layers of the Tear Film" Optometry and Vision Science, vol. 76, No. 1, Jan. 1999, 14 pages (pp. 19-32).

Khamene, Ali, et al., "A Spectral-Discrimination Method for Tear-Film Lipid-Layer Thickness Estimation from Fringe Pattern Images" IEEE Transactions on Biomedical Engineering, vol. 47, No. 2, Jan. 2000, 10 pages (pp. 249-258).

King-Smith, P. Ewen, et al., "The Thickness of the Human Precorneal Tear Film Evidence from Reflection Spectra" Investigative Ophthalmology & Visual Science, vol. 41, No. 11, Oct. 2000, 12 pages (pp. 3348-3359).

Loveridge, Ron, "Effective Management of Induced Dry Eye Syndrome with Soft CLs" www.optometry.co.uk, Apr. 2000, 4 pages (pp. 35-38).

Sullivan, David A., et al., "Androgen Influence on the Meibomian Gland" Investigative Ophthalmology & Visual Science, vol. 41, No. 12, Nov. 2000, 11 pages (pp. 3732-3742).

Hamilton, Dr. Roy C., "Ocular Explosion; a Dreaded Complication of Ophthalmic Regional Anaesthesia" Ophthalmic Anaesthesia News, Issue 4, Apr. 2001, 43 pages.

Korb, Donald R. O.D., et al., "Comparison of Fluorescein Break-Up Time Measurement Reproducibility Using Standard Fluorescein Strips Versus the Dry Eye Test (DET) Method" pCornea, vol. 20(8), Philadelphia, 2001, 8 pages.

Fenimore, C.P., et al., "Assessment of Resolution and Dynamic Range for Digital Cinema" National Institute of Standards and Technology, Gaithersburg, MD, Circa 2002, 8 pages.

Finlayson, Graham, et al., "Hue that is Invariant to Brightness and Gamma" School of Information Systems, University of East Anglia, Norwich, United Kingdom, Circa 2002, 9 pages (pp. 303-312).

Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).

King-Smith, P. Ewen, et al., "Evaporation from the Human Tear Film Studied by Interferometry" Lacrimal Gland, Tear Film, and Dry Eye Syndromes 3, Kluwer Academic/Plenum Publishers, 2002, 5 pages (pp. 425-429).

Korb, Donald R., "Alleviation of Computer-Induced Eye Discomfort Syndrome and Associated Lipid Layer Changes" Lacrimal Gland, Tear Film, and Dry Eye Syndromes 3, Kluwer Academic/Plenum Publishers, 2002, 6 pages (pp. 501-506).

Korb, Donald R., et al., "The Effects of Anionic and Zwitterionic Phospholipids on the Tear Film Lipid Layer" Lacrimal Gland, Tear Film, and Dry Eye Syndromes 3, Kluwer Academic/Plenum Publishers, 2002, 5 pages (pp. 495-499).

Miano, Fausto, et al., "Interface Properties of Simplified Tear-Like Fluids in Relation to Lipid and Aqueous Layers Composition" Lacrimal Gland, Tear Film, and Dry Eye Syndromes 3, Kluwer Academic/Plenum Publishers, 2002, 13 pages (pp. 405-417).

Nichols, Jason J., OD, MS, FAAO, et al., "Evaluation of Tear Film Interference Patterns and Measures of Tear Break-Up Time" Optometry and Vision Science, vol. 79, No. 6, Jun. 2002, 7 pages (pp. 363-369).

Nichols, Jason J., "The Thickness of the Post-Lens Tear Film Measured by Interferometry" Lacrimal Gland, Tear Film, and Dry Eye Syndromes 3, Kluwer Academic/Plenum Publishers, 2002, 5 pages (pp. 929-933).

Thai, Lee Choon, BSc, MCOptom, et al., "Contact Lens Drying and Visual Performance: The Vision Cycle with Contact Lenses" Optometry and Vision Science, vol. 79, No. 6, Jun. 2002, 8 pages (pp. 381-388).

Tomlinson, Alan, et al., "Reliability of Measurements of Tear Physiology" Lacrimal Gland, Tear Film, and Dry Eye Syndromes 3, Kluwer Academic/Plenum Publishers, 2002, 9 pages (pp. 1097-1105).

Begley, Carolyn, G., et al., "Relationship Between Symptom Profile and Clinical Signs Among Dry Eye Patients" Circa 2003, 1 page.

Begley, Carolyn, G., et al., "The Relationship Between Habitual Patient-Reported Symptoms and Clinical Signs among Patients with Dry Eye of Varying Severity" Investigative Ophthalmology & Visual Science, vol. 44, No. 11, Nov. 2003, 9 pages (pp. 4753-4761).

Foulks, Gary N., MD, FACS, et al., "Meibomian Gland Dysfunction: A Clinical Scheme for Description, Diagnosis, Classification, and Grading" Clinical Science, The Ocular Surface, vol. 1, No. 3, Jul. 2003, 20 pages (pp. 107-126).

Goto, Eiki, et al. "Computer-Synthesis of an Interference Color Chart of Human Tear Lipid Layer, by a Colorimetric Approach" Investigative Ophthalmology & Visual Science, vol. 44, No. 11, Nov. 2003, 5 pages (pp. 4693-4697).

Goto, Eiki, et al., "Kinetic Analysis of Tear Interference Images in Aqueous Tear Deficiency Dry Eye Before and After Punctual Occlusion" Investigative Ophthalmology & Visual Science, vol. 44, No. 5, May 2003, 9 pages (pp. 1897-1905).

Isreb, MA, et al., "Correlation of Lipid Layer Thickness Measurements with Fluorescein Tear Film Break-Up Time and Schirmer's Test" Eye, vol. 17, 2003, 5 pages (pp. 79-83).

Nichols, Jason J., OD, MS, MPH, et al., "The Effect of Eye Closure on the Post-Lens Tear Film Thickness During Silicone Hydrogel Contact Lens Wear" Cornea, vol. 22(6), 2003, 6 pages (pp. 539-544).

Nichols, Jason J., et al., "Thickness of the Pre- and Post-Contact Lens Tear Film Measured in Vivo by Interferometry" Investigative Ophthalmology & Visual Science, vol. 44, No. 1, Jan. 2003, 10 pages (pp. 68-77).

Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.

Author Unknown, "Blepharitis" The Eye Digest, The Dry Eye Research Center, University of Illinois at Chicago, 2003, 3 pages.

Yokoi, Norihiko, et al., "Non-Invasive Methods of Assessing the Tear Film" Experimental Eye Research, vol. 78, Elsevier Ltd., 2003, 9 pages (pp. 399-407).

Di Pascuale, Mario A., M.D., et al., "Sequential Changes of Lipid Tear Film after the Instillation of a Single Drop of a New Emulsion Eye Drop in Dry Eye Patients" American Academy of Ophthalmology, vol. 111, 2004, 9 pages (pp. 783-791).

Goto, Eiki, M.D., "Quantification of Tear Interference Image; Tear Fluid Surface Nanotechnology" Cornea, vol. 23, Suppl. 1, Nov. 2004, 5 pages (pp. S20-S24).

Nichols, Jason J., et al., "The Impact of Hydrogel Lens Settling on the Thickness of the Tears and Contact Lens" Investigative Ophthalmology & Visual Science, vol. 45, No. 8, Aug. 2004, 6 pages (pp. 2549-2554).

Thai, Lee Choon, BSc, MCOptom, et al., "Effect of Contact Lens Materials on Tear Physiology" Optometry and Vision Science, vol. 81, No. 3, Mar. 2004, 11 pages (pp. 194-204).

van Veen, R. L. P., et al., "Determination of VIS-NIR Absorption Coefficients of Mammalian Fat, with Time- and Spatially Resolved Diffuse Reflectance and Transmission Spectroscopy" Circa 2004, 3 pages.

Yokoi, Norihiko, et al., "New Instruments for Dry Eye Diagnosis" Seminars in Ophthalmology, vol. 20, 2004, 8 pages (pp. 63-70).

Di Pascuale, Mario A., M.D., et al., "Lipid Tear Deficiency in Persistent Dry Eye After Laser in Situ Keratomileusis and Treatment Results of New Eye-Warming Device" J Cataract Refract. Surg., vol. 31, ASCRS and ESCRS, Elsevier Inc., 2005, 9 pages (pp. 1741-1749).

Dubra, Alfredo, et al., "Double Lateral Shearing Interferometer for the Quantitative Measurement of Tear Film Topography" Applied Optics, vol. 44, No. 7, Mar. 2005, 9 pages (pp. 1191-1199).

Garcia-Resua, C., et al., "Clinical Evaluation of the Tears Lipid Layer in a Young University Population" Rev. Esp. Contact, vol. 12, 2005, 6 pages.

Iskander, D. Robert, PhD., et al., "Applications of High-Speed Videokeratoscopy" Clinical and Experimental Optometry, vol. 88, vol. 4, Jul. 2005, 9 pages (pp. 223-231).

Korb, Donald R., O.D., et al., "Lid Wiper Epitheliopathy and Dry Eye Syndrome" Eye & Contact Lens, vol. 31 (1), 2005, 7 pages (pp. 2-8).

Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).

Bartlett, Hannah, et al. "New Perspectives on the Investigation and Treatment of Dry Eye Syndrome—Part 1" Optician, vol. 231, No. 6038, Feb. 2006, 9 pages (pp. 27-37).

Garcia, Julius, "Research Report; Tear Film Measurement" Report No. 09354231-1; Aug. 2006, 46 pages.

Gravely, Ben, "Observations from TFA3" Aug. 2006, 4 pages.

King-Smith, P. Ewen, et al., "Interferometric Imaging of the Full Thickness of the Precorneal Tear Film" J. Opt. Soc. Am. A, vol. 23, No. 9, Sep. 2006, 8 pages (pp. 2097-2104).

Lui, Haixia, MD, et al., "Temporal Progression and Spatial Repeatability of Tear Breakup" Optometry and Vision Science, vol. 83, No. 10, Oct. 2006, 8 pages (pp. 723-730).

Lorentz, Holly Irene, "Lipid Deposition on Hydrogel Contact Lenses" Master's Thesis, University of Waterloo, Ontario, Canada, 2006, 175 pages.

Matsumoto, Yukihiro, et al., "Efficacy of a New Warm Moist Air Device on Tear Functions of Patients with Simple Meibomian Gland Dysfunction" Cornea, vol. 25, No. 6, Jul. 2006, 1 page.

Ohashi, Yoshiki, et al., "Laboratory Findings in Tear Film Analysis" Clinica Chimica Acta 369, 2006, 12 pages (pp. 17-28).

Patel, Sudi, PhD, FCOptom, FAAO, et al., "Tear Meniscus Height, Lower Punctum Lacrimale, and Tear Lipid Layer in Normal Aging" Optometry and Vision Science, vol. 83, No. 10, Oct. 2006, 9 pages (pp. 732-739).

Shiel, William C., Jr., MD, FACP, FACR, "Sjogren's Syndrome" MedicineNet.com, http:www.medicinenet.com, Sep. 2006, 3 pages.

Szczesna, Dorota H. et al., "Interferometric Measurements of the Tear Film Irregularities on the Human Cornea" Proc. of SPIE, vol. 5959, Circa 2006, 10 pages.

Tomlinson, Alan, et al., "Tear Film Osmolarity: Determination of a Referent for Dry Eye Diagnosis" Investigative Ophthalmology & Visual Science, vol. 47, No. 10, Oct. 2006, 7 pages (pp. 4309-4315).

Wang, Jianhua et al., "Relationships between Central Tear Film Thickness and Tear Menisci of the Upper and Lower Eyelids" Investigative Ophthalmology & Visual Science, vol. 47, No. 10, Oct. 2006, 7 pages (pp. 4349-4355).

Author Unknown, "*Keratoconjunctivitis sicca*" Wikipedia, http://en.wikipedia.org/wiki/keratoconjunctivitis_sicca, Nov. 2006, 4 pages.

Author Unknown, "Thermographic Camera" Wikipedia, http://en.wikipedia.org/wiki/thermographic_camera, Sep. 2006, 4 pages.

Cruz, Daniele, "Dry Eye Syndrome More Widespread than Predicted" Ocular Surgery News, U.S. Edition, May 2007, 1 page.

Cruz, Daniele, "Surgeon: Early Treatment Key to Avoiding Dry Eye Progression" Ocular Surgery News, U.S. Edition, May 2007, 1 page.

Fouks, Gary N., MD, FACS, "The Correlation Between the Tear Film Lipid Layer and Dry Eye Disease" Major Review, Survey of Ophthalmology, vol. 52, No. 4, Jul.-Aug. 2007, 6 pages (pp. 369-374).

Korb, Donald R., OD, et al., "A Device to Standardize and Quantify the Force Used to Diagnose Meibomian Gland Obstruction and Dysfunction" 2007, 1 page.

Korb, Donald R., OD, et al., "A New Device for the Diagnosis of Meibomian Gland Dysfunction and Obstruction" 2007, 1 page.

Kronemyer, Bob, "Dry Eye Experts Unveil New Treatment Guidelines, Terminology" Ocular Surgery News, U.S. Edition, May 2007, 1 page.

Yokoi, N, et al., "Development of Automated Rheological Analysis for Tear Film Lipid Layer Spread Using the Cross-Correlation Method" Association for Research in Vision and Ophthalmology, 2007, 1 page.

Borchman, Douglas, et al., "Temperature-Induced Conformational Changes in Human Tear Lipids Hydrocarbon Chains" Biopolymers, vol. 87, No. 2-3, Jun. 13, 2007, pp. 124-133 (10 pages).

Szczesna, Dorota H., et al., "Robust estimation of tear film surface quality in lateral shearing interferometry," Journal of Biomedical Optics, vol. 14, No. 6, Nov./Dec. 2009, 4 pages.

Szczesna, Dorota H., et al., "Assessing Tear Film on Soft Contact Lenses With Lateral Shearing Interferometry," Eye & Contact Lens: Science & Clinical Practices, vol. 37, Issue 6, Nov. 2011, pp. 342-347.

Boyer, Kim L. et al., "Resilient Subclass Discriminant Analysis with Application to Prelens Tear Film Interferometry," Proceedings, Lecture Notes in Computer Science, vol. 6718/2011, MCPR, Cancun, Mexico, Jun. 29-Jul. 2, 2011, pp. 1-11.

De Paiva, Cintia S., et al., "Diagnostic Approaches to Lacrimal Keratoconjunctivitis," Dry Eye and Ocular Surface Disorders, New York, NY: Marcel Dekker, 2004, pp. 269-270.

Unknown, "Tomey's RT-7000 is new and improved," Instruments—New Product Gallery, Vision Care Product News (VCPN), Jul. 2008, 1 page.

Unknown, Honan Balloon Intraocular Pressure Reducer with Valve—Complete, Ambler Surgical, Ambler Product No. HBC-120, Nov. 19, 2007, http://www.amblersurgical.com/store/product.cfm/pID:2456_5961E, 1 page.

Fanning, Gary L., M.D., "Ocular Compression: A Review," OASIS Newsletter, Ophthalmic Anesthesia Society, Summer 2006, http://www.eyeanesthesia.org/newsletter/pdf/oasis_summer06.pdf, 7 pages.

Unknown, "Tearscope Plus: Introduction and guided tour to the benefits of the Keeler Tearscope-plus," Keeler Instruments, bon Optic, created Jan. 24, 2006, www.bon.de/download/TearscopeE.pdf, 22 pages.

McGrath, Dermot, "Iris diaphragm IOLs safe and effective in treating aniridia," EuroTimes, European Society of Cataract & Refractive Surgeons, May 2007, http://www.escrs.org/PUBLICATIONS/EUROTIMES/07MAY/IRISDIAPHRAGMIOLS.PDF, p. 42.

Oculus, "Oculus Keratograph 5M Der Revolutionar," Oculus, 2 pages, date unknown.

Bon, "Meibographie: mit der PHOENIX Analyse-Software," bon Optic Vertriebsgesellschaft mbH, Nov. 2011, 4 pages.

Yokoi, N. et al., "Relationship between tear volume and tear meniscus curvature," Arch. Ophthalmology, vol. 122, Sep. 2004, pp. 1265-1269.

European Search Report issued Jan. 20, 2012, for European Patent Application No. 11183259.8, 11 pages.

TEAR FILM MEASUREMENT

RELATED APPLICATION

This application is a Continuation-In-Part of U.S. patent application Ser. No. 11/820,664 filed Jun. 20, 2007 now U.S. Pat. No. 7,758,190.

FIELD OF THE INVENTION

This invention relates generally to the field of measurement of the tear film thickness on the precorneal surface of the eye and more particularly, to the measurement of the thickness of the outermost layer of the tear film, i.e., the lipid layer.

BACKGROUND OF THE INVENTION

The human precorneal tear film is comprised of three primary layers, each of which serves a specific function. The innermost layer of the precorneal tear film provides a protective environment for the superficial epithelial cells of the cornea and helps protect against microbes and foreign bodies. The outer surface of the precorneal tear film is the primary refracting surface of the eye. Its surface tension helps to smooth this surface, thus improving the optical quality of the image ultimately impacting the retina. Additionally, the precorneal tear film provides a lubricating function during blinking. These structures are often disrupted in dry eye conditions, which are some of the most common ophthalmic disorders seen by eye-care practitioners. Dry eye disorders and/or disease can lead to premature breakup of the tear film after a blink, leading to damage of the superficial epithelium which may result in discomfort and be manifested as optical blur. In addition, the ability of a patient to wear contact lenses is a direct function of the quality and quantity of the tear film, and dry eye disorders and/or disease therefore has a significant impact on contact lens wear parameters.

The precorneal tear film is comprised of an inner mucin layer, a middle aqueous layer, and an outermost thin lipid layer. Various treatments are used in an attempt to alleviate dry eye symptoms. For example, it has been proposed to treat certain dry eye conditions by the application of heat and pressure to unclog meibomian glands, or with pharmaceutical methods to unclog meibomian glands and to stimulate tear production.

Notwithstanding the foregoing, it has been a long standing and vexing problem for clinicians and scientists to objectively demonstrate an improvement in the precorneal tear film thickness at the conclusion of the proposed treatment. Further, many promising treatments for dry eye have failed to receive approval from the United States Food and Drug Administration due to the inability to demonstrate clinical effectiveness to the satisfaction of the agency.

In response to the foregoing long felt need, various methods of measuring the thickness of the precorneal tear film, and specifically the lipid layer thereof have been proposed. For example, Korb, one of the inventors of this invention provided an overview and background of his invention of a specular reflection microscope system that allowed quantification of the tear film lipid layer thickness based on the interference colors of the lipid layer. This system included a hemi-cylindrical broad spectrum illumination source with heat absorbing filters, a binocular microscope with a Zeiss beam-splitter providing 70% light to a high resolution video camera, a VHS recorder, and a high resolution 20-inch color monitor. Following calibration with Eastman Kodak color reference standards (Wratten filters), the static and dynamic appearance of the lipid layer was observed before and after blinking. During the observation period, the subject was instructed to blink naturally while gazing at a fixation target. For purposes of quantization and standardization, a specific region of the tear film was designated for analysis. This area encompassed a zone approximately one mm above the lower meniscus to slightly below the inferior pupillary margin, averaging 7-8 mm wide and 2.5 mm in height. The dominant color of the specularly reflected light within this designated area was used as the basis for assigning lipid layer thickness values. Thickness values were assigned to specific colors on the basis of prior work on tear film lipid layer interference colors (McDonald, 1969; Nom.; 1979; Guilon, 1982; Hamano et al., 1982) and are summarized in Table 1. To confirm the lipid layer thickness values assigned to each subject's tear film lipid layer, recordings were independently graded by two observers masked as to subject identity. (Korb, D R, Baron D F, Herman J P, et al., Tear Film Lipid Layer Thickness as a Function of Blinking, *Cornea* 1994:13:354-9). While the foregoing apparatus was effective in measuring improved lipid layer thickness, measurement inaccuracies were nevertheless introduced into the system. Working backwards, the color monitor had to be provided with a sufficient input signal to enable the lipid layer to be imaged on to the monitor screen. The foregoing thus required a minimum illumination to be provided to the slit lamp, of which 70% was directed to the high resolution video camera. This, in turn, dictated the minimum amount of light required to illuminate the corneal surface. Thus, the amount of light required to make the foregoing system operational was not optimum as it interfered with the naturally occurring tear film as the heat generated by the light caused tear film evaporation. Further, the amount of light required to make the system functional caused some degree of reflex tearing.

Another apparatus for measuring the tear film is disclosed in European Patent Application EP 0 943 288 assigned to Kowa Company, Ltd. of Japan. The application discloses an apparatus for the non-contact measurement of the quantity of lacrimal fluid collected on the lower eyelid. According to the invention, tear volume is calculated from a measurement of the volume of fluid pooled at the lid eye meniscus. While knowledge of the total volume of fluid may be of some use to eye-care practitioners, it does not specifically measure the lipid layer thickness or its improvement as the result of a particular treatment regimen.

U.S Pat. No. 4,747,683 to Marshall G. Doane discloses a Method and Device for in Vivo Wetting Determinations wherein a contact lens is illuminated with coherent light and the pre-lens tear film is imaged in such a way as to form an interference pattern. The image formed thereby is recorded and the tear film thickness is determined by correlating the interference bands of the recorded image. A coherent light source and a camera are focused at the pre-lens film to image specularly reflected light from the front and rear surfaces of the tear film. A film motion analyzer provides numerical coordinates of interference bands, and a microprocessor analyses the coordinates to provide a quantitative measure of lens position or wetting characteristics. Again, while knowledge of the tear film thickness covering the contact lens surface may be useful in the context of contact lens fitting, the Doane apparatus does not specifically measure lipid layer thickness on the natural eye.

Another instrument that purports to measure tear film lipid layer thickness is the Tearscope Plus manufactured by Keeler Instruments Inc., of Broomall, Pa. and Berkshire, UK. More specifically, the Tearscope is a hand-held or slit lamp mounted device that comprises a tubular housing which contains a coaxially mounted cylindrical light source. The interior bore of the housing is covered with a cylindrical diffuser plate that diffuses the light. In use, the eye-care practitioner places one end of the tube proximate the patient's eye thus illuminating the whole eye, including the pupil, and observes the interference patterns on the pupil surface through the opposite end of the tube. The color of the interference pattern generated by blinking is then correlated to tear film thickness. The Tearscope is not without its inherent drawbacks and deficiencies as the process by which the eye is illuminated and the measurement is made introduces error which is diagnostically unacceptable. For example, the proximity of the illuminator to the eye surface when combined with the light intensity required to obtain a viewable interference pattern can cause reflex tearing. In addition, the illumination system employed illuminates the entire eye, including the pupil. Thus, light from the Tearscope is directed on to the retinal surface which, in turn causes a proprioceptive response which also skews measurement accuracy.

In view of the foregoing, it is an object of the present invention to provide a method and apparatus that overcomes the drawbacks and deficiencies of the prior art.

Another object of the present invention is to provide a method and apparatus that allows the accurate measurement of the thickness of the lipid layer component of the precorneal tear film.

A further object of the present invention is to provide a method and apparatus wherein the lipid layer thickness of the precorneal tear film may be measured without the introduction of reflex tearing.

A still further object of the present invention is to provide a method and apparatus that enhances contrast and thereby the observability and measurablity of the lipid layer thickness of the precorneal tear film.

Yet another object of the present invention is to provide a method and apparatus for measuring the lipid layer thickness of the precorneal tear film using a low level of light in order to minimize tear film evaporation that can alter the measurement.

Another object of the present invention is to provide a method and apparatus for measuring the lipid layer thickness of the precorneal tear film wherein the patient is comfortable during the examination.

Another object of the present invention is to provide a method and apparatus for measuring the lipid layer thickness of the precorneal tear film that minimizes light entering the pupil to minimize reflex tearing and proprioceptive responses that can alter the measurement.

SUMMARY OF THE INVENTION

In accordance with the foregoing, the invention comprises a method for measuring the thickness of the lipid layer component of the precorneal tear film on the surface of an eye after distribution of the lipid layer subsequent to blinking. Light is directed to the lipid layer of a patient's eye by use of an illuminator which produces specularly reflected light rays. The illuminator is a broad spectrum, large area lambertian light source covering the visible region, the rays of which are specularly reflected from the lipid layer and undergo constructive and destructive interference in the lipid layer. The specularly reflected light is collected and focused such that the interference patterns on the tear film lipid layer are observable. An output signal is produced that is representative of the specularly reflected light which is suitable for further analysis, such as projection on to a high resolution video monitor or analysis by or storage in a computer. Alternatively, the interference patterns of the specularly reflected light may be directly observed by the clinician and recorded. In order to facilitate ease of measurement, the patient's head may be positioned on an observation platform, for example, a slit lamp stand, when the illuminator directs light to the lipid layer of the patient's eye.

In a first embodiment of the invention, the illuminator is sized to show the interference pattern of the lipid layer over the whole eye, (termed herein the "whole eye illuminator"), with the provision that the intensity of the light entering the pupil and striking the retina are below the threshold at which appreciable measurement error is introduced, i.e., the reflex tear and proprioceptive responses are not activated. Observation of the interference pattern in the preferred embodiment is through an opening in the illuminator.

In a second embodiment of the invention, the illuminator is sized to show the interference pattern of the lipid layer below the pupil, (termed herein the "half eye illuminator"), such that the intensity of the light entering the pupil is extremely low, thus avoiding the introduction of virtually all system-induced inaccuracy. Observation of the interference pattern in this second embodiment is from above the illuminator.

BRIEF DESCRIPTION OF THE DRAWINGS

These and other features will be understood with reference to the figures, in which.

DETAILED DESCRIPTION OF THE PREFERRED EMBODIMENTS

Figure 1:
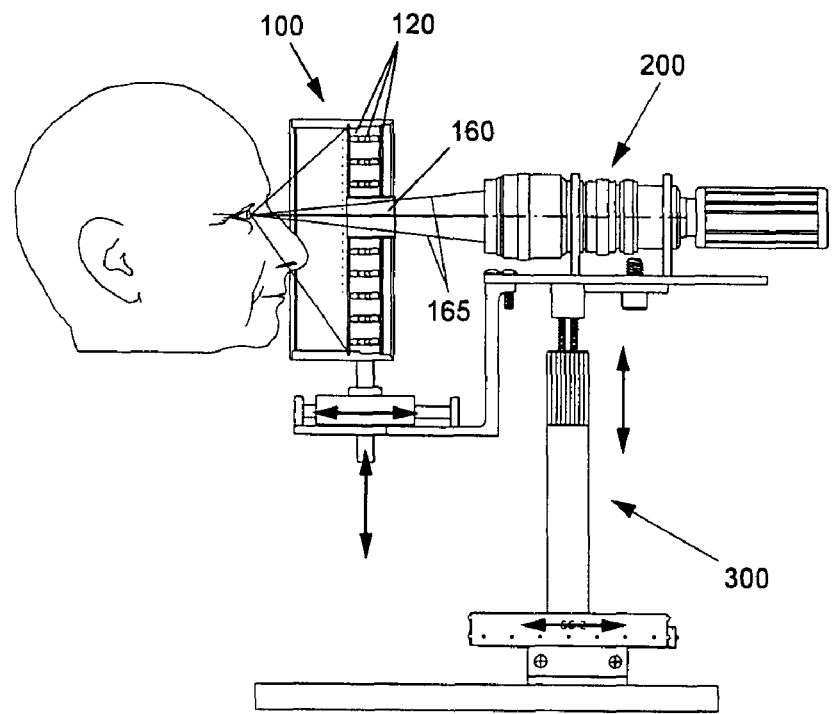
FIG. 1 is a side view of the tear film analyzer according to the present invention mounted to a stand with a patient positioned for viewing of interference fringes on the lipid layer of the eye. The illuminator portion is shown as a vertical cross section through the center.

While the present invention will be described more fully hereinafter with reference to the accompanying drawings, in which particular embodiments are shown, it is to be understood at the outset that persons skilled in the art may modify the invention herein described while still achieving the favorable results of this invention. Accordingly, the description which follows it to be understood as a broad teaching disclosure directed to persons of skill in the appropriate arts and not as limiting upon the present invention.

In a first embodiment best shown in FIGS. 1, 2 and 6-8, referred to herein as the "full eye illuminator", the present invention broadly comprises illuminating the lipid layer of the patient's eye and observing the light specularly reflected therefrom. A second embodiment best shown in FIGS. 3a, 3b, 5a-5c and 9-11, referred to herein as the "half eye" illuminator is shown. The mode of operation of the two embodiments is substantially identical and they will therefore be described together using the same reference numerals and where differences between the embodiments occur, they will be discussed.

Figure 12:
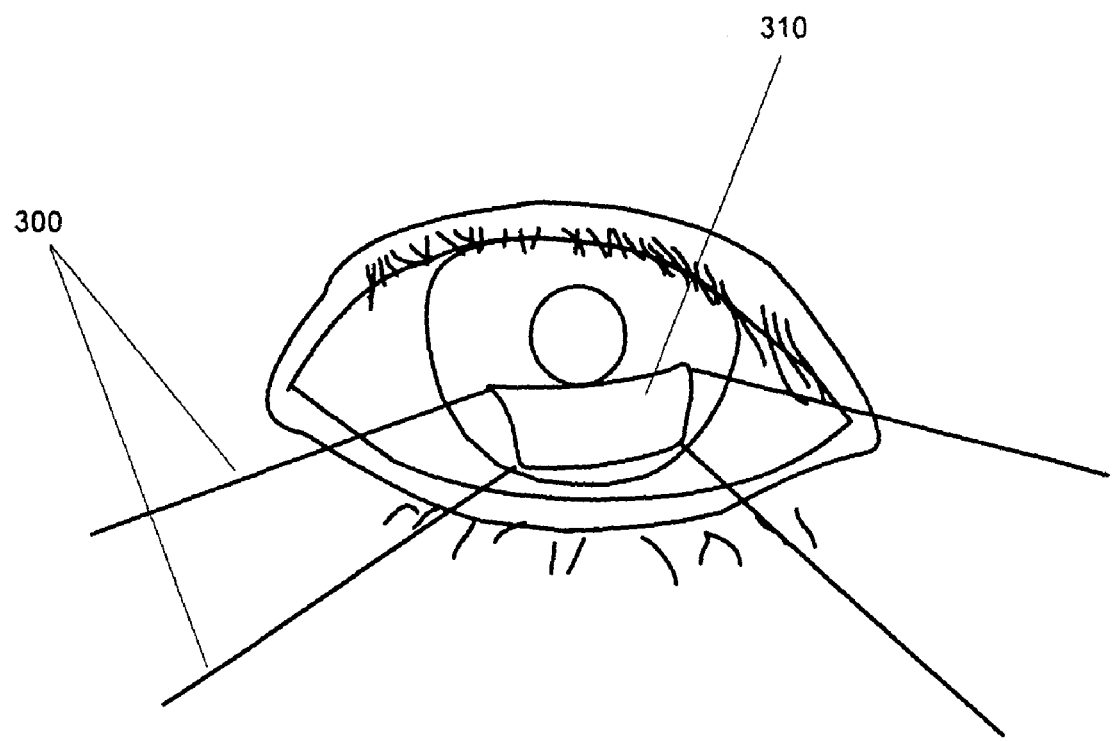
FIG. 12 is a front view of the surface of an eye and illustrating schematically the area defined by the extreme lambertion rays wherein interference patterns are viewable.

The lipid layer of a patient's eye is illuminated with an illuminator 100 and comprises a large area broad spectrum light source covering the visible region. The illuminator 100 is a lambertian emitter adapted to be positioned in front of the eye on a stand 300. As employed herein the terms "lambertion surface" and "lambertian emitter" are defined to be a light emitter having equal intensity in all directions. The light source comprises a large surface area emitter, arranged such that rays emitted from the emitter are specularly reflected from the lipid layer and undergo constructive and destructive interference in the lipid layer. An image of this surface is the backdrop over which the interference image is seen and it should be as spatially uniform as possible. The illuminator 100 illuminates a large area of the face which creates a 2.5 mm high by 5 mm long viewable area centered beneath the pupil 310 (see FIG. 12) which is adequate for lipid layer thickness determination and correlation to dry eye. By "viewable area" it is meant the active area that satisfies the criteria for viewing interferences fringes; i.e., approximately 2.5 mm×7 mm for the half eye illuminator. Full-eye illumination, excluding the pupil area, reveals additional information about the whole eye pattern of lipid distribution.

The geometry of the illuminator 100 can be most easily understood by starting from the camera lens and proceeding forward to the eye and then to the illuminator. The fundamental equation for tracing ray lines is Snell's law:

$$N_1 \sin \varnothing_1 = N_2 \sin \varnothing_2, \quad\quad 1)$$

where N is the refractive index of the medium containing the ray, and ø is angle of the ray relative to the normal from the surface. For a reflected ray that doesn't enter the lipid layer, $N_1=N_2$, and $$\varnothing_1 = \varnothing_2 \quad\quad 2)$$

Under these conditions, Snell's law reduces to the classical "angle of incidence is equal to the angle of reflectance" statement.

Figure 2:
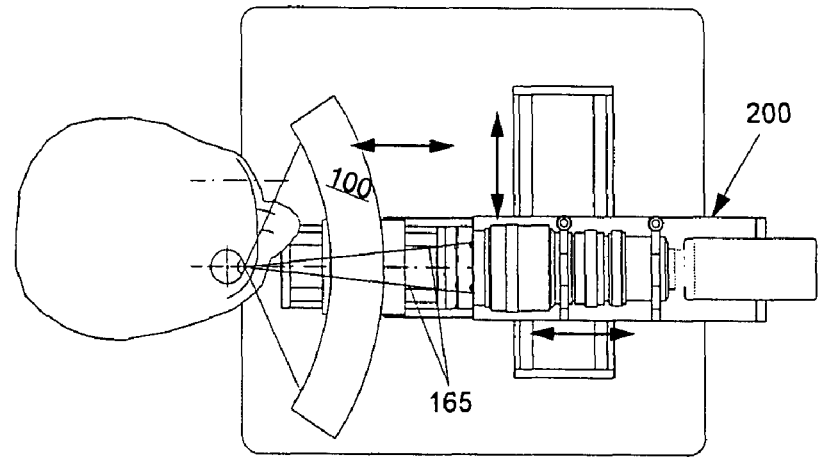
FIG. 2 is a plan view of the tear film analyzer according to the present invention mounted to a stand with a patient positioned for viewing of interference fringes on the lipid layer of the eye.
Figure 3A:
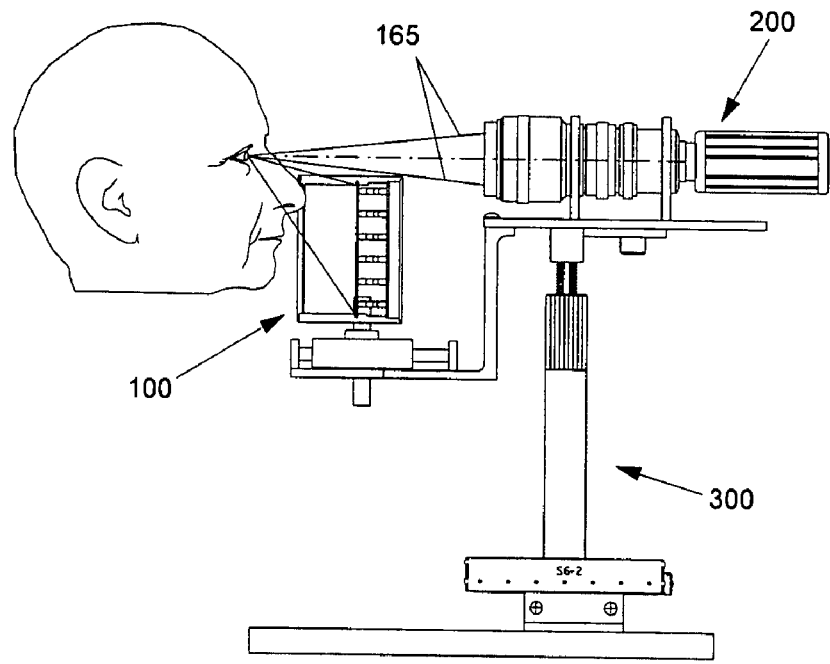
FIG. 3a is a side view of a second embodiment of the tear film analyzer according to the present invention mounted to a stand with a patient positioned for viewing of interference fringes on the lipid layer of the eye. The illuminator portion is shown as a vertical cross section through the center.
Figure 3B:
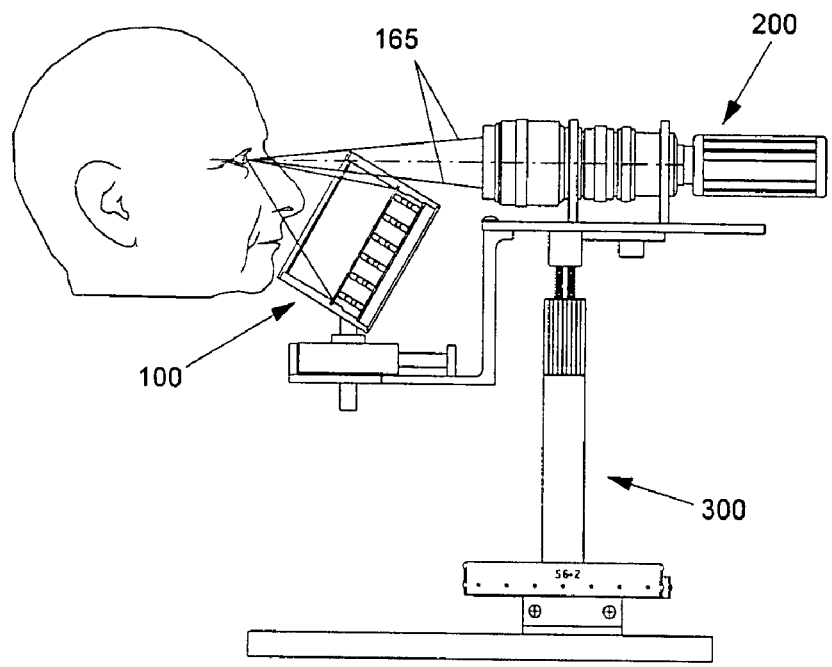
FIG. 3b is a side view of the second embodiment of the tear film analyzer according to the present invention mounted to a stand and tilted with a patient positioned for viewing of interference fringes on the lipid layer of the eye. The illuminator portion is shown as a vertical cross section through the center.
Figure 4A:
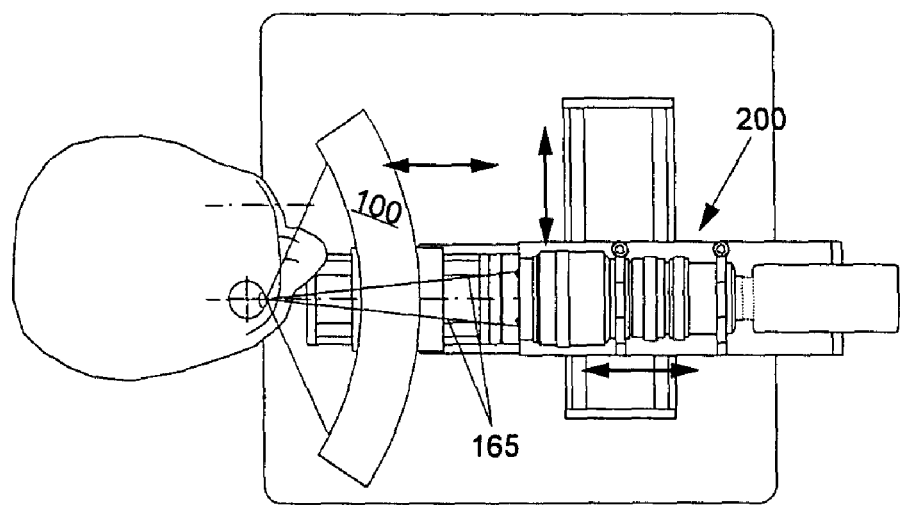
FIG. 4a is a plan view of the second embodiment of the tear film analyzer according to the present invention mounted to a stand with a patient positioned for viewing of interference fringes on the lipid layer of the eye.
Figure 4B:
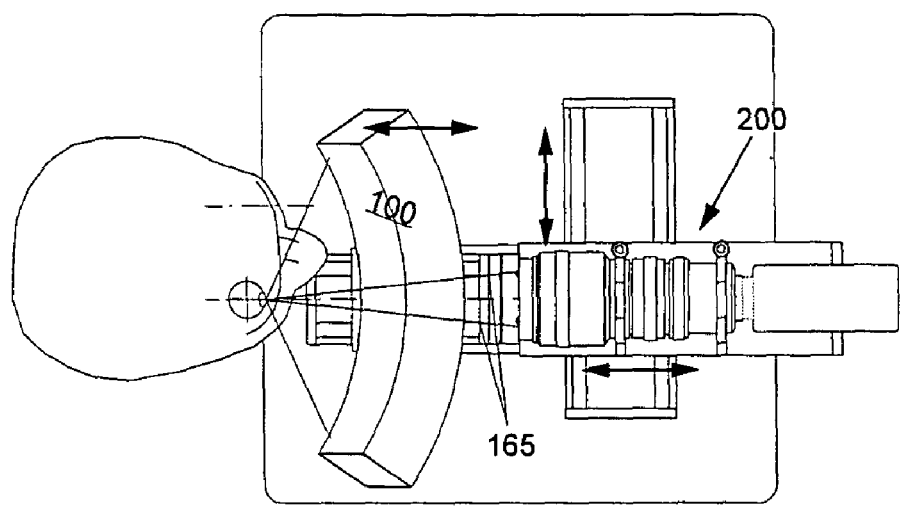
FIG. 4b is a plan view of the second embodiment of the tear film analyzer according to the present invention mounted to a stand and tilted with a patient positioned for view of interference fringes on the lipid layer of the eye.
Figure 5A:
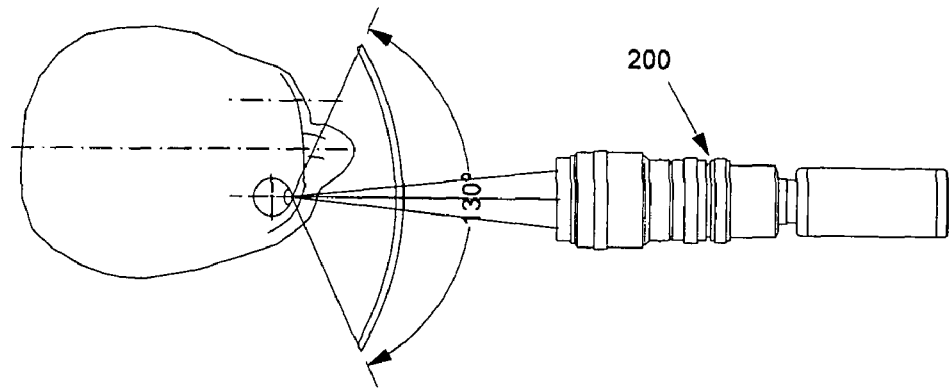
FIG. 5a is a plan view of the second embodiment of the tear film analyzer according to the present invention illustrating the illuminator surface that produces the outer edges of the viewable area of interference fringes.
Figure 5B:
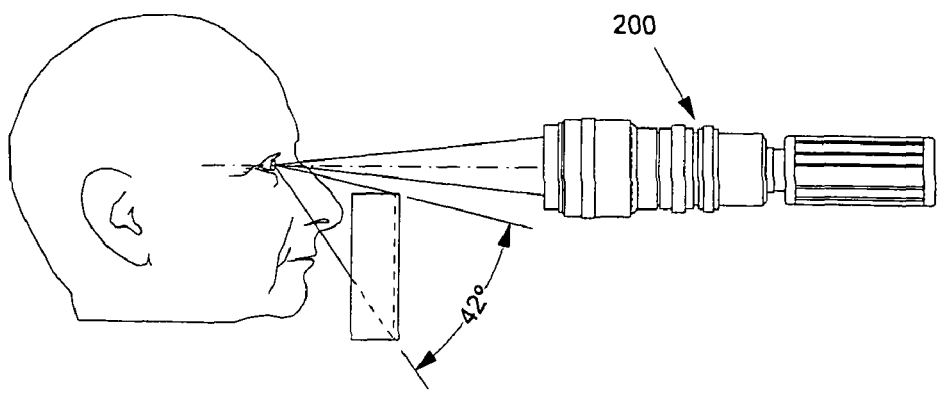
FIG. 5b is a side view of the second embodiment of the tear film analyzer according to the present invention illustrating the illuminator surface vertically positioned below the plane of the pupil and showing the outer edges of the viewable area of interference fringes.
Figure 5C:
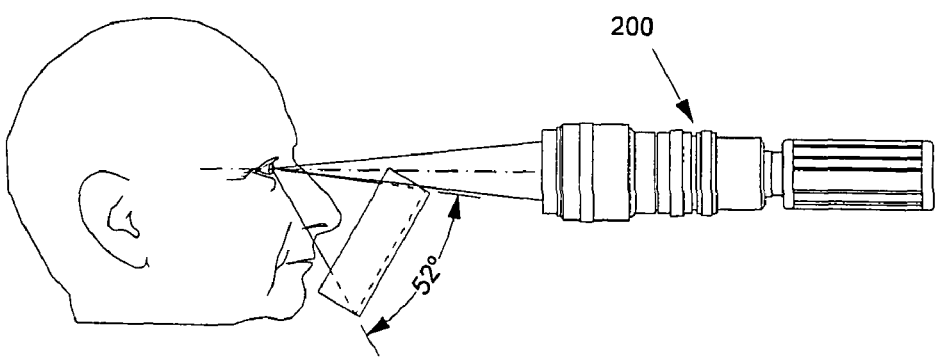
FIG. 5c is a side view of the second embodiment of the tear film analyzer according to the present invention illustrating the illuminator surface positioned below the plane of the pupil and tilted at an angle and showing the outer edges of the viewable area of interference fringes.
Figure 6:
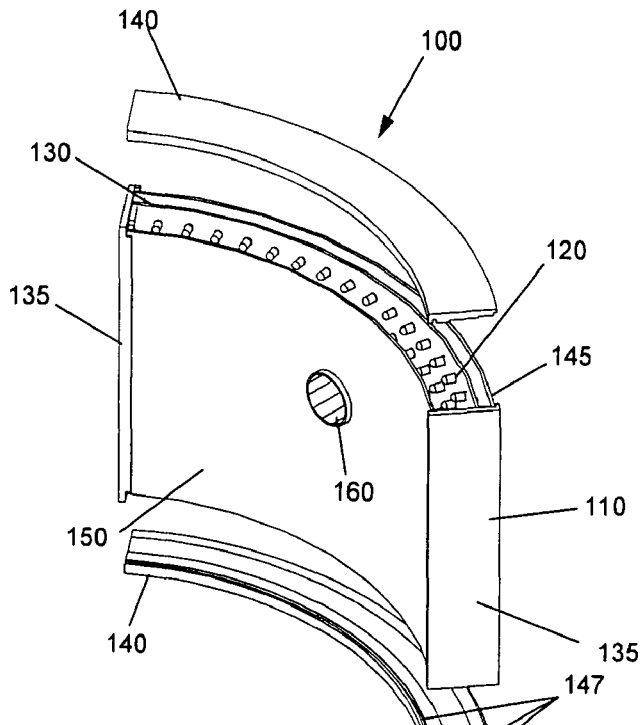
FIG. 6 is a perspective view, partially exploded, of the full eye illuminator according to the present invention.
Figure 7:
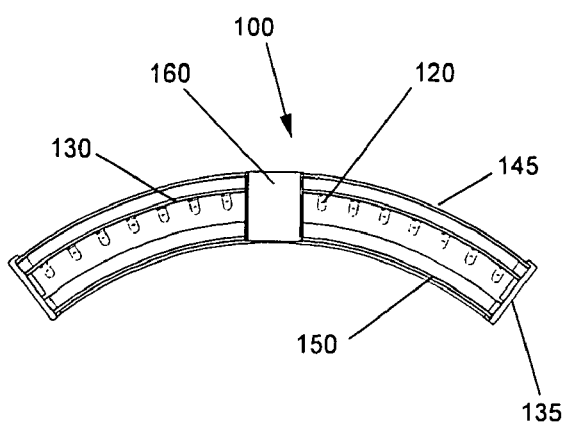
FIG. 7 is a plan view, sectioned horizontally through the center of the viewing hole of the full eye illuminator according to the present invention.
Figure 8:
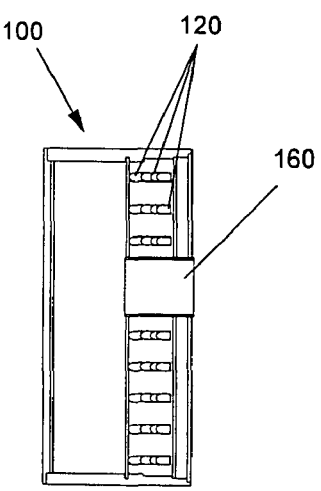
FIG. 8 is an end view, sectioned vertically through the center of the full eye illuminator according to the present invention.
Figure 9:
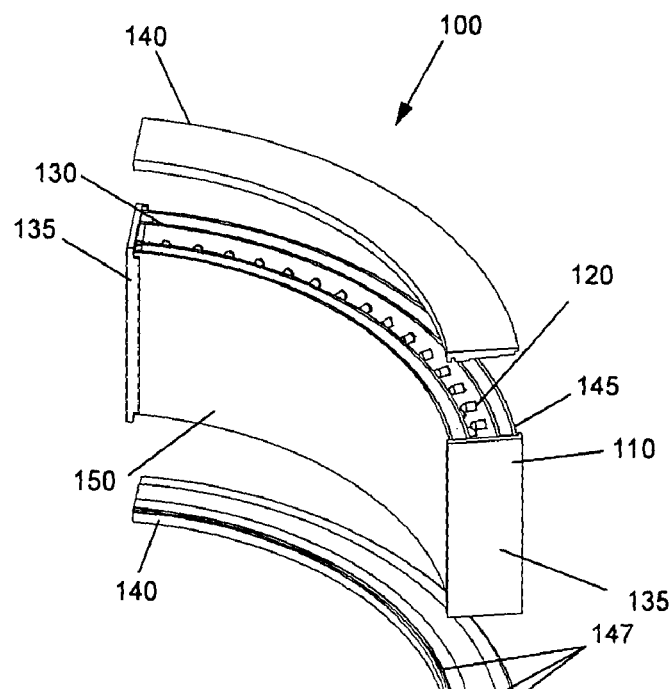
FIG. 9 is a perspective view, partially exploded of the half eye illuminator according to the present invention.
Figure 10:
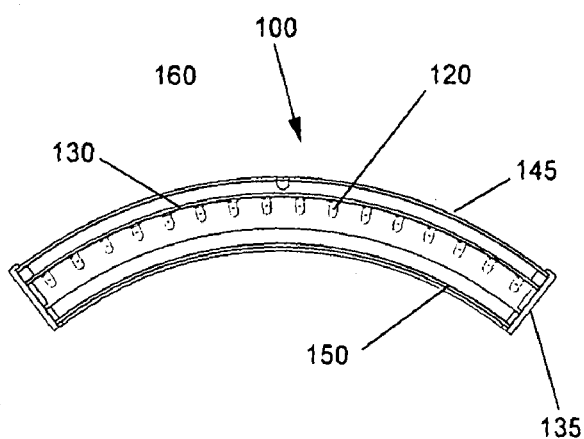
FIG. 10 is a plan view with the top removed of the half eye illuminator according to the present invention.
Figure 11:
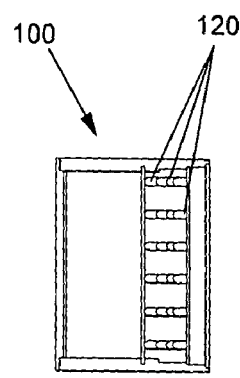
FIG. 11 is an end view, sectioned vertically through the center of the half eye illuminator according to the present invention.

According to the present method, it is necessary to determine only the extreme rays (the ones at the outermost boundary of the desired viewing area) to define the area of the illuminator. Since the surface of that portion of the eye to be examined is approximately spherical, a line drawn from the camera lens (or the observer's eye) to the edge of the viewing area on the observed eye will reflect at the same angle on the other side of the line normal to the eye surface at the point of intersection of the line with the eye. When the half eye illuminator used, it may be tilted to better accommodate the nose and illuminate a larger area of the inferior lipid layer. Notwithstanding the foregoing, experimentation using the half eye illuminator has shown that a tilt of 10° to as much as 30° is still functional. Returning now to the full eye illuminator, as best shown in FIGS. 1 and 2, it will be seen that facial features block some rays from reaching the surface of the eye. The nose, cheeks, eyebrows, and eyelids block rays, causing shadows on the eye surface. Positioning the illuminator for maximum area exposure is unique to each patient's facial structure. The mechanical dimensions (height and width) of the illuminator may be extended to cover the biometric range of facial features of the target population.

The illuminator 100 is a broad spectrum light source covering the visible region between about 400 nm to about 700 nm. In the model that was constructed, high efficiency, white Light Emitting Diodes ("LEDs") 120 were used that have a 50° forward projection angle, 2500 mcd typical intensity, and 5 mm diameter (part number NSPW510CS, available from Nichia Corporation, Wixom, Mich.). Other LEDs could be added to the present invention to enhance the spectral width in the near UV or near IR regions. The light emitting array platform 130 (FIGS. 6, 7) into which the LEDs are mounted had a curved surface, subtending an arc of approximately 130° from the optical axis of the eye (see FIG. 5a). Approximately 96 LEDs spaced apart in a grid pattern with 6 rows and 16 columns were connected in parallel/series combinations and connected to an appropriate power supply, well known to those skilled in the art and therefore, not shown. A housing is formed around the LED array platform 130 by a pair of side panels 135, bottom and top panels 140, rear panel 145 and the diffuser means or diffuser 150. The respective diffuser 150, LED platform 130, and rear panel 145 are flexible and fit within grooves 147 located in the top and bottom panels 140 and the end pieces 135. The entire assembly is snapped together and the side panels 135 are then screwed to top and bottom panels 140. While the illumination means 100 illustrated in the figures is curved or arcuate and has a radius of 7.620 inches from the center of the eye under examination, it could be flat as long as it subtends 130° around the eye. A curved surface is more efficient in doing this, as the geometry yields a smaller device which is easier for the practitioner to use in a clinical setting.

The total power radiated from the illuminator 100 must be kept to a minimum to prevent accelerated tear evaporation. In addition, air currents generated by heating or cooling systems can also cause excess evaporation and must be minimized (preferably eliminated) to maintain measurement accuracy. The brightness, or intensity, measured in $\mu W/mm^2$, entering the pupil can cause reflex tearing, squinting, and other visual discomforts, all of which affect measurement accuracy. For a full-eye illuminator, the curved lambertian emitter includes a centrally positioned hole defining an opening 160 through which the means for collecting and focusing the specularly reflected light, i.e., a camera, eye, or other lens 200, is positioned. The opening 160 in the center substantially prevents direct illumination from entering the pupil of the test eye. While less than optimal, the opening 160 could be located in other parts of the illuminator. The other eye, however, has the full light intensity entering the pupil. If the illumination intensity is low enough, the exposed eye does not react. The exposed eye may also be occluded with a mask, or the illuminator may be segmented so that parts of the surface are not illuminated. The half-eye illuminator stops below the centerline of the eye and does not directly illuminate either pupil or stated otherwise, light rays can only enter the pupil obliquely and do not impinge on the retina. The current full-eye illuminator has a brightness or illumination intensity of between about 3 $\mu W/mm^2$ and 15 $\mu W/mm^2$ with about 4.5 $\mu W/mm^2$ at the surface of the illuminator being preferred, which is held 1-2 inches from the eye. The total radiated power is less than 1 W and preferably no more than 400 mW. Brightness above about 6 $\mu W/mm^2$ becomes uncomfortable to the second eye if it enters the pupil so as to impinge directly on the retina. The front surface of the illuminator is the lambertian emitter, i.e., all points on the extended illuminator surface are lambertian emitters, and comprises a flexible white translucent acrylic plastic sheet 150 approximately 1/16 inch thick that serves the function of diffusing the light emitted from a plurality of LED point sources and transforming them into the uniform Lambertian emitter.

In order to prevent alteration of the proprioceptive senses and reduce heating of the tear film, it is important to minimize the incident power and intensity on the eye and thus, the step of collecting and focusing the specularly reflected light is carried out by a high sensitivity color camera 200. The video camera, slit lamp or other observation apparatus 200 is positioned in opening 160 and is also mounted on stand 300 as shown in FIG. 2 or in the case of the half eye illuminator positioned above the emitter as per FIGS. 3a and 3b. Detailed visualization of the image patterns requires collecting the specularly reflected light and focusing the specularly reflected light such that the interference patterns from the lipid layer are observable. Good digital imaging requires a CCD video camera having a resolution of up to 1280×1024 pixels and at least 15 Hz frame rate to show the progression of lipid interference patterns as they spread across the eye. The AVT Dolphin 145C, 2/3 inch, CCD camera with 6.45 μm square pixels meets the requirements and outputs a signal representative thereof which may serve as the input signal to any one of a number of devices such as a video monitor (preferably high resolution) or a computer for analysis and/or archiving purposes.

The lens system employed in the instant tear film analyzer images a 15-40 mm dimension in the sample plane (the eye) onto the active area of the CCD detector (e.g. 13 mm horizontal dimension for a 2/3 in. CCD). The lens f-number should be as low as practical to capture maximum light and minimize the illumination power needed for a good image. The lens chosen for the half-eye and full-eye systems is the Navitar Zoom 7000 close focus zoom lens for 2/3in. format CCDs. At lower magnification (25-40 mm field of view), the eye and lids can be examined to observe the relationship of the blink to the lipid layer thickness. A more detailed analysis of the lipid layer can be obtained with a slightly higher magnification showing a 15-25 mm field of view.

The lipid layer thickness is not uniform and is classified on the basis of the most dominant color present in the interference pattern. It is believed that the lipid layer for most individuals cannot exceed 180 nm, and since thicker lipid layers provide better protection from evaporation than thinner lipid layers, thicker lipid layers provide greater protection against the development of dry eye states. Thinner lipid layers are associated with dry eye states and dry eye symptoms, particularly if the lipid layer thickness is less than 75 nm.

The present system displays the interference patterns from white light incident on the lipid layer film. The relation between the colors of the interference pattern and the lipid layer thickness (LLT) are shown in Table 1.

TABLE 1

| Color | LIPID LAYER THICKNESS (nm) | Letter Grade |
|---|---|---|
| Blue | 180 | A |
| Blue/Brown | 165 | A− |
| Brown/Blue | 150 | B+ |
| Brown | 135 | B |
| Brown/Yellow | 120 | B− |
| Yellow/Brown | 105 | C+ |
| Yellow | 90 | C |
| Grey/Yellow | 75 | C− |
| Grey | 60 | D+ |
| Grey/White | 45 | D |
| White | 30 | F |

Extensive research has established that thicker films are indicated by a blue and brown color, mid-thickness films are indicated by a yellow color, thinner films are indicated by a grey-yellow color, and very thin films exhibit a gray scale of different densities with white representing the thinnest. It is believed in color photometry, brown can be obtained in an additive process by mixing small intensities of red and green, or orange and blue, basically the opposite ends of the visible light spectrum. Alternatively, brown can be obtained in a subtractive process by filtering out the central yellow-green colors from the white spectrum, leaving a blue-orange mix.

It has not been verified why the wavelengths of light observed in the interference film are inverse to the film thickness, but extensive clinical testing has led the inventors to the belief and the theory that destructive interference is the dominant process. The closer the wavelength is to the film thickness, the greater the interference, so yellow-red interference will have the strongest effect in a thicker film. However, thicker films appear blue, so it is postulated that red wavelengths are removed from the incident light spectrum by destructive interference and the reflected light appears blue.

For a thinner film, blue will have a stronger interference. Since the thinner films appear reddish, it is assumed that the blue is removed by destructive interference. From this, we assume that the color seen is the broadband surface reflection with the dominant interference color band removed. That is, interference subtracts the portion of the spectrum indicative of the film thickness from the reflected light, leaving the complementary colors. This is the best explanation known to the inventors of how brown is obtained from a system of this type. It must be noted that the thickness of the lipid layer on the eye is much smaller than all the wavelengths of visible light. Therefore, full wavelength interference patterns are believed not to be possible. For fractional wavelengths, ($\lambda/2n$, $n=1,2\ldots$) the intensity in the interference pattern decreases rapidly as n increases and the ability to differentiate weak interference patterns from the background decreases accordingly.

When the lipid film thickness falls below about 90 nm, no color is seen in the image generated by the present apparatus (employing the current LED light source), only gray of varying density. It is presumed that violet and ultraviolet interference effects predominate at this thickness, but since they are absent from the incident spectrum, no color can be seen. Any interference remaining over the visible light spectrum is so weak due to the very small fraction ($\lambda/2n$, $n>5$) that full-spectrum reflection and absorption effects dominate and no particular color can be seen. Broadband destructive interference in the 60-75 nm layers gives way to broadband constructive interference at the thinnest layer ($<=30$ nm).

In summary, it is believed that the present invention demonstrates the results of subtractive colors, where subtracting the blue end from white light leaves a reddish tint, subtracting the center (yellow-green) from the spectrum leaves a brownish tint, and subtracting orange-red leaves a blue tint. Because all the interference patterns are fractional wavelengths, and therefore relatively weak in intensity, the images are not strongly saturated. Image enhancement techniques therefore assume a higher importance for good visibility. Film thickness below about 90 nm can be determined by gray scale analysis.

Should the use of real time or high speed data transfer and large storage volumes be required for a given application, the use of a means for recording the output signal representative of the specularly reflected light (video output signal) such as a high performance computer system would be needed. As employed herein, the term "real time" is defined as data transfer, storage and retrieval at a rate required for image generation that the observer requires for a subjectively satisfactory viewing experience. For viewing the motion of the lipid layer interference pattern after blinking a minimum of about 15 frames per second is satisfactory for seamless motion perception. Depending upon settings, the camera can create 1.4-3.9 MB images at 15 per second, or 21-57 MB/sec which must be processed by the computer for storage, display, or computation. At this rate, one minute of recording requires 1.26-3.42 GB of storage. Given the presently available technology, it is not reasonable to store recording sessions in RAM, so the data from the camera must be streamed directly to a storage system sized to meet the anticipated volume of data. For example, 500 GB of storage could record 147-397 tests of one minute duration. Various forms of data management could be applied to reduce the storage requirements, including image size, compression, and minimizing recording time adequate to good diagnostics.

The software to operate the camera, capture the images, store and retrieve image files, and execute chosen calculations on the data is critical to the success of the system. Relevant specifications are:

The mechanical system consists of components to position the patient's head, position the illuminator and camera, focus the camera, and switch position between eyes.

Current ophthalmic chin rests are adequate for positioning and restraining the head. They include vertical (Z axis) adjustment.

A movable frame positions the camera and illuminator opposite the patient's face. The illuminator and camera move together in a gross manner, but the illuminator has an independent X and rotational motions for accommodating different facial geometries. Switching from eye to eye requires moving the whole camera/illuminator frame away from the patients face (X motion) and horizontally to line up with the second eye (Y motion). Focusing the camera requires fine control of X motion, and vertical Z motion is required to accommodate differences in patient eye positions. A classical slit lamp biomicroscope stand incorporates most of these motions, and have added angular motions not needed in the present system.

FIGS. 1, 2, 3*a*-3*b* illustrate the full-eye system. A typical examination session proceeds as follows:

Presets: The vertical relationship between the camera and the illuminator is set. For a half-eye illuminator, the camera position is just enough higher than the illuminator top edge that the image contains no edge effects. When using the full-eye illuminator, the camera is positioned coaxially with the hole through the illuminator. The camera/illuminator position should not need adjusting thereafter.

Patient examination:
1. The patient is seated and asked to place their chin on the chin rest. The chin rest is adjusted (Z axis) for the comfort of the patient. The patient is asked to hold their forehead against the forehead rest.
2. The frame holding the camera & illumination is positioned on the axis of the first eye and brought close enough for rough focus on the skin.
3. The frame is adjusted for vertical and horizontal centering, and then moved forward for fine focusing.
4. The illuminator is adjusted forward and back, and rotated for best illumination of the eye. Repeat fine focus as necessary. The patient is asked to look directly at the center or top center of the camera lens. Instructions are given to the patient for blinking regimens by the diagnostician. It will be noted that measurement is taken when the patient is not blinking, but that this interval is between the previous blink and before the next blink. Therefore, as employed herein the terms "after blinking" and "before blinking" are somewhat interchangeable as they both refer to the substantially non-eyelid moving period of time "between blinks".
5. The images are viewed and recorded as desired.
6. The frame may be pulled away from the patient (to clear the nose) and moved horizontally to the next eye. Steps 2.-5 are repeated.

The system could be fully motorized and operated in manual, semi-autonomous, or autonomous modes, depending upon the sophistication of the control software. A fully automatic system would adjust the mechanical stand, focus the camera, record the motion of the lipid film, calculate various measurements of the film structure, report an assessment of the quality of the lipid film, and record the data in the patient's record file.

The invention having been thus disclosed, diverse changes and variation in the apparatus and method will occur to those skilled in the art, and all such changes and modifications are intended to be within the scope of the invention, as set forth in the following claims:

That which is claimed is:
1. A method for measuring the thickness of the lipid layer on the surface of a patient's eye after distribution of the lipid layer subsequent to blinking comprising the steps of:
illuminating the lipid layer of a patient's eye with a broad spectrum light source illuminator in the visible region and being a lambertian emitter such that the rays from the light source are specularly reflected from the lipid layer and undergo constructive and destructive interference in the lipid layer thereby producing interference patterns; and an imaging device for observing the specularly reflected light such that the interference patters on the tear film lipid layer are observable.

2. The method according to claim 1 wherein the illuminator comprises an arcuate emitter and wherein the surface of the lambertian emitter is substantially parallel to the surface of the eye.

3. The method according to claim1 wherein the specularly reflected light is observed through a hole defining an opening in the illuminator.

4. The method according to claim 3 wherein the opening in the illuminator allows for observation of the specularly reflected light from behind said illuminator.

5. The method according to claim 3 further including the steps of collecting and focusing the specularly reflected light and the step of generating an output signal representative thereof operatively associated with the opening.

6. The method according to claim 5 further including the step of recording the output signal representative of the specularly reflected light.

7. The method according to claim 6 wherein the step of recording the output signal representative of the specularly reflected light records in real time.

8. The method according to claim 5 wherein the step of collecting and focusing the output signal is produced by use of a camera lens system.

9. The apparatus according to claim 6 wherein the recording is selected from the group of recording devices consisting of computer memory, video cassette recording devices, analog recording devices and digital recording devices.

10. The method according to claim 1 wherein the specularly reflected light is observed when the patient's head is positioned on an observation platform.

11. The method according to claim 2 wherein the arcuate emitter is constructed and arranged such that the light rays emitted therefrom strike the surface of the eye such that Snell's Law is satisfied and produces an observable area of interference on the surface of the eye.

12. The method according to claim 1 wherein said illuminator further includes a plurality of spaced apart light emitting diodes adapted to emit light in the visible region; and a diffuser for diffusing the light emitted by the respective light emitting diodes positioned between the light emitting diodes and the surface of the eye and further, wherein the diffuser is arcuate such that the light rays emitted therefrom strike the surface of the eye such that Snell's law is satisfied with respect to the acceptance angle of the camera lens system to produce an observable area of interference on the eye.

13. The method according to claim 11 wherein the light rays that generate the visible viewing area of interference are substantially normal to the surface of the eye.

14. The method according to claim 1 wherein said illuminator has a total radiated power of less than 1 W.

15. A method for measuring the thickness of the lipid layer on the surface of an eye after distribution of the lipid layer subsequent to blinking comprising the steps of:

illuminating the lipid layer of a patient's eye with a broad spectrum light source illuminator in the visible region and being a lambertian emitter such that the light source is specularly reflected from the lipid layer and undergoes constructive and destructive interference in the lipid layer thereby producing interference patters in the tear film and further, wherein the total light emitted from the surface of the illuminator is less than 10 $\mu W/mm^2$; and observing the specularly reflected light.

16. The method according to claim 15 wherein the illuminator further includes an arcuate emitter and wherein the surface of the emitter is substantially parallel to the surface of the eye.

17. The method according to claim 15 wherein the specularly reflected light is observed through a hole defining an opening in the illuminator.

18. The method according to claim 17 wherein the opening in the illuminator allows for observation of the specularly reflected light from behind said illuminator.

19. The method according to claim 17 further including the step of collecting and focusing the specularly reflected light and the step of generating an output signal representative thereof operatively associated with the opening.

20. The method according to claim 19 further including the step of recording the output signal representative of the specularly reflected light.

21. The method according to claim 20 wherein the step of recording the output signal representative of the specularly reflected light records in real time.

22. The method according to claim 19 wherein the steps of collecting and focusing is produced by the use of a camera lens system.

23. The method according to claim 20 wherein the step of recording is selected from the group of recording devices consisting of computer memory, video cassette recording devices, analog recording devices and digital recording devices.

24. The method according to claim 15 wherein the specularly reflected light is observed when the patient's head is positioned on an observation platform.

25. The method according to claim 15 wherein the arcuate emitter is constructed and arranged such that the light rays emitted therefrom strike the surface of the eye such that Snell's law is satisfied and an observable area of interference is produced on the eye.

26. The method according to claim 15 wherein the illuminator further includes a plurality of spaced apart light emitting diodes adapted to emit light in the visible region; and diffusing the light emitted by the respective light emitting diodes and further, wherein the illuminator is arcuate such that the light rays emitted from the lambertian emitter strike the surface of the eye such that Snell's law is satisfied with respect to the acceptance angle of said camera lens system to produce an observable area of interference on the eye.

27. The method according to claim 25 further including the step of collecting the specularly reflected light and focusing the specularly reflected light generates an output signal representative thereof.

28. The method according to claim 25 wherein the illuminator has a total radiated power of less than 1 W.

29. The method according to claim 25 wherein the light rays that generate the visible viewing area of interference are essentially normal to the surface of the eye.

30. A method for measuring the thickness of the lipid layer on the surface of a patient's eye after distribution of the lipid layer subsequent to blinking comprising the steps of:

illuminating the lipid layer of a patient's eye with broad spectrum light source illuminator in the visible region and being a uniform illumination lambertian emitter such that the light source is specularly reflected from the lipid layer and undergoes constructive and destructive interference in the lipid layer; and further wherein the illuminator illuminates the patients face, but wherein only an area below the pupil satisfies Snell's law; and observing the area of interference in specularly reflected light on the tear film lipid layer below the pupil.

31. The method according to claim 30 further including the steps of collecting and focusing the specularly reflected light such that the interference patterns on the tear film lipid layer are observable.

32. The method according to claim 30 wherein the illuminator illuminates an area of the patient's eye and wherein the area having viewable interference fringes is located below the pupil.

33. The method according to claim 32 wherein the area having viewable interference fringes is an area of at least 12.5 $mm^2$.

34. The method according to claim 30 wherein the illuminator has a total illumination intensity of less than that which would induce reflex tearing or cause a proprioceptive response to occur.

35. The method according to claim 34 wherein the illuminator has a total illumination intensity of between about 1 $\mu W/mm^2$ and 15$\mu W/mm^2$ at the surface of the illuminator.

36. The method according to claim 32 wherein the specularly reflected light is observed when the patient's head is positioned on an observation platform.

37. The method according to claim 30 further including the step of recording the observable area of interference of the specularly reflected light.

38. The method according to claim 37 wherein the step of recording the observable are of interference records in real time.

39. The method according to claim 37 wherein the step of recording is selected from the group of recording devices consisting of computer memory, video cassette recording devices, analog recording devices and digital recording devices.

40. The method according to claim 31 wherein the step of collecting and focusing the specularly reflected light generates an output signal representative thereof.

41. The method according to claim 30 wherein the illuminator comprises an array of light emitting diodes and a diffuser positioned between the respective diode array and the lipid layer of the tear film.

42. The method according to claim 41 where the diffuser is arcuate such that the light rays emitted from the lambertian emitter strike the surface of the eye such that Snell's law is satisfied and an observable area of interference is produced on the eye.

43. A method for measuring the thickness of the lipid layer on the surface of an eye after distribution of the lipid layer subsequent to blinking comprising the steps of:

illuminating the lipid layer of a patient's eye with a broad spectrum light source illuminator in the visible region and being uniform illumination lambertian emitter such that the light source is specularly reflected from the lipid layer and undergoes constructive and destructive interference in the lipid layer and wherein the light emitted from the illuminator travels directly to the lipid layer without reflection and strikes the lipid layer; and collecting and focusing the specularly reflected light such that the interference patterns on the tear film lipid layer are observable.

44. The method according to claim 43 wherein the illuminator illuminates an area of the patient's eye and wherein the area having viewable interference fringes is located below the pupil.

45. The method according to claim 43 wherein the area having viewable interference fringes in an area of at least 12.5 $mm^2$.

46. The method according to claim 43 wherein the illuminator has a total illumination intensity of less than what which would induce reflex tearing or cause a proprioceptive response to occur.

47. The method according to claim 43 wherein the illuminator has a total illumination intensity of between about 1 $\mu W/mm^2$ and 15 $\mu W/mm^2$ at the surface of the illuminator.

48. The method according to claim 43 wherein the illuminator has a total radiated power of less than about 1 W.

49. The method according to claim 44 wherein the specularly reflected light is observed when the patient's head is positioned on an observation platform.

50. The apparatus according to claim 43 further including the step of recording the observable area of interference of the specularly reflected light.

51. The apparatus according to claim 50 wherein the step of recording the observable area of interference records in real time.

52. The apparatus according to claim 51 wherein the step of recording is selected from the group of recording devices selected from the group consisting of computer, video cassette recording devices and digital recording devices.

53. The method according to claim 44 wherein the step of collecting and focusing the specularly reflected light generate an output signal representative thereof.

54. The method according to claim 43 wherein the illuminator comprises an array of light emitting diodes and a diffuser positioned between the respective diode array and the lipid layer of the tear film.

55. The method according to claim 54 where the diffuser is arcuate such that the light rays emitted from the lambertian emitter strike the surface of the eye such that Snell's law is satisfied and an observable area of interference is produced on the eye.

* * * * *